United States Patent
Kim et al.

(10) Patent No.: US 11,940,446 B2
(45) Date of Patent: Mar. 26, 2024

(54) STRUCTURE FOR MICROBE DETECTION, MANUFACTURING METHOD THEREFOR, AND MICROBE DETECTION METHOD USING SAME STRUCTURE FOR MICROBE DETECTION

(71) Applicant: INDUSTRY-UNIVERSITY COOPERATION FOUNDATION HANYANG UNIVERSITY ERICA CAMPUS, Ansan-Si (KR)

(72) Inventors: Jong-Ho Kim, Ansan-si (KR); Tae Woog Kang, Ansan-si (KR); Sin Lee, Ansan-si (KR); In Jun Hwang, Ansan-si (KR); Ju Hee Han, Ansan-si (KR)

(73) Assignee: INDUSTRY-UNIVERSITY COOPERATION FOUNDATION HANYANG UNIVERSITY ERICA CAMPUS, Ansan-Si (KR)

( * ) Notice: Subject to any disclaimer, the term of this patent is extended or adjusted under 35 U.S.C. 154(b) by 843 days.

(21) Appl. No.: 17/044,878

(22) PCT Filed: May 16, 2018

(86) PCT No.: PCT/KR2018/005603
§ 371 (c)(1),
(2) Date: Oct. 2, 2020

(87) PCT Pub. No.: WO2019/194352
PCT Pub. Date: Oct. 10, 2019

(65) Prior Publication Data
US 2021/0102941 A1    Apr. 8, 2021

(30) Foreign Application Priority Data

Apr. 3, 2018 (KR) .................. 10-2018-0038652

(51) Int. Cl.
*G01N 33/569* (2006.01)
*C01B 19/00* (2006.01)
(Continued)

(52) U.S. Cl.
CPC ....... *G01N 33/56916* (2013.01); *C01B 19/00* (2013.01); *C01G 41/00* (2013.01);
(Continued)

(58) Field of Classification Search
CPC .................................................. G01N 33/569
See application file for complete search history.

(56) References Cited

U.S. PATENT DOCUMENTS 9,388,458 B2   7/2016   Tseng et al.
9,757,342 B2   9/2017   Paik et al.

FOREIGN PATENT DOCUMENTS

KR   10-2013-0039672   4/2013
KR   10-2014-0071968   6/2014
(Continued)

OTHER PUBLICATIONS

Grayfer et al. "Colloidal 2D nanosheets of MoS2 and other transition metal dichalcogenides through liquid-phase exfoliation" Advances in Colloid and Interface Science, 2017, 245, 40-61. (Year: 2017).*

(Continued)

*Primary Examiner* — Peter F Godenschwager
(74) *Attorney, Agent, or Firm* — Finch & Maloney PLLC

(57) ABSTRACT

A method for manufacturing a structure for microbe detection comprises the steps of: reacting nitrilotriacetic acid (NTA) and an acid anhydride to prepare a first compound; chelation of metal ions to the first compound to prepare a second compound; binding the second compound and a microbe detector to prepare a third compound; and mixing an exfoliated transition metal-dichalcogenide (TMD) compound and the third compound to prepare a structure for
(Continued)

microbe detection, in which the metal ions of the third compound are bound with the transition metal-dichalcogenide compound.

7 Claims, 33 Drawing Sheets

(51) Int. Cl.
  *C01G 41/00* (2006.01)
  *G01N 21/64* (2006.01)
  *G01N 21/65* (2006.01)

(52) U.S. Cl.
  CPC ........ *C01B 19/007* (2013.01); *G01N 21/6486* (2013.01); *G01N 21/65* (2013.01); *G01N 2333/245* (2013.01); *G01N 2333/255* (2013.01)

(56) References Cited

FOREIGN PATENT DOCUMENTS

| KR | 10-2014-0117249 | 10/2014 |
| KR | 10-1771355 | 8/2017 |
| KR | 10-1795969 | 11/2017 |

OTHER PUBLICATIONS

Hu et al., "Two-dimensional transition metal dichalcogenide nanomaterials for biosensing applications", Mater. Chem. Front., vol. 1, pp. 24-36 (2017).
Park et al., "M-DNA/Transition Metal Dichalcogenide Hybrid Structure-based Bio-FET sensor with Ultrahigh Sensitivity", Scientific Reports 6:35733 (2016).
Park et al., "n- and p-Type Doping Phenomenon by Artificial DNA and M-DNA on Two-Dimensional Transition Metal Dichalcogenides", ACS Nano 8(11):11603-13 (2014).

* cited by examiner

[Fig. 1]
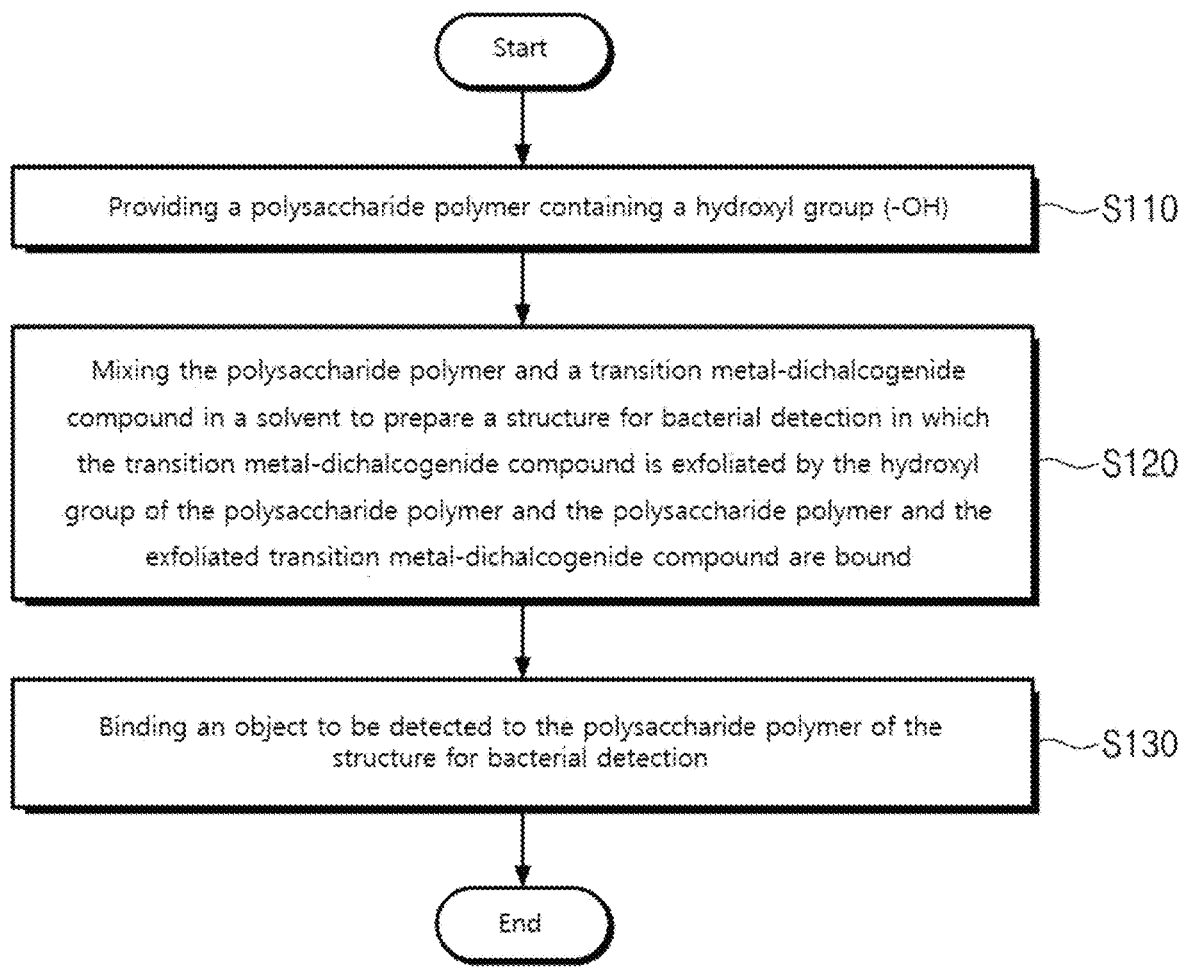

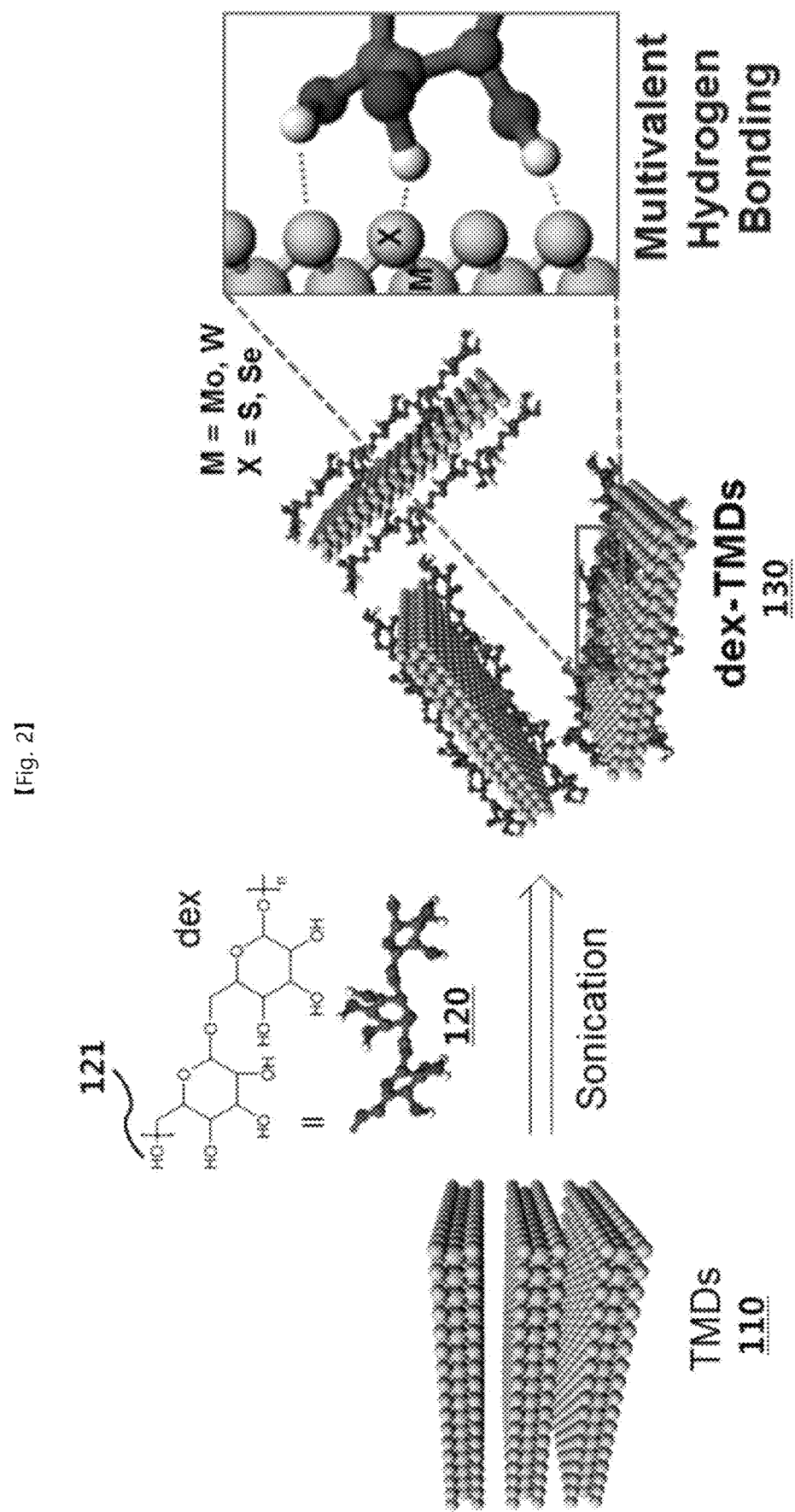
[Fig. 2]

[Fig. 3]
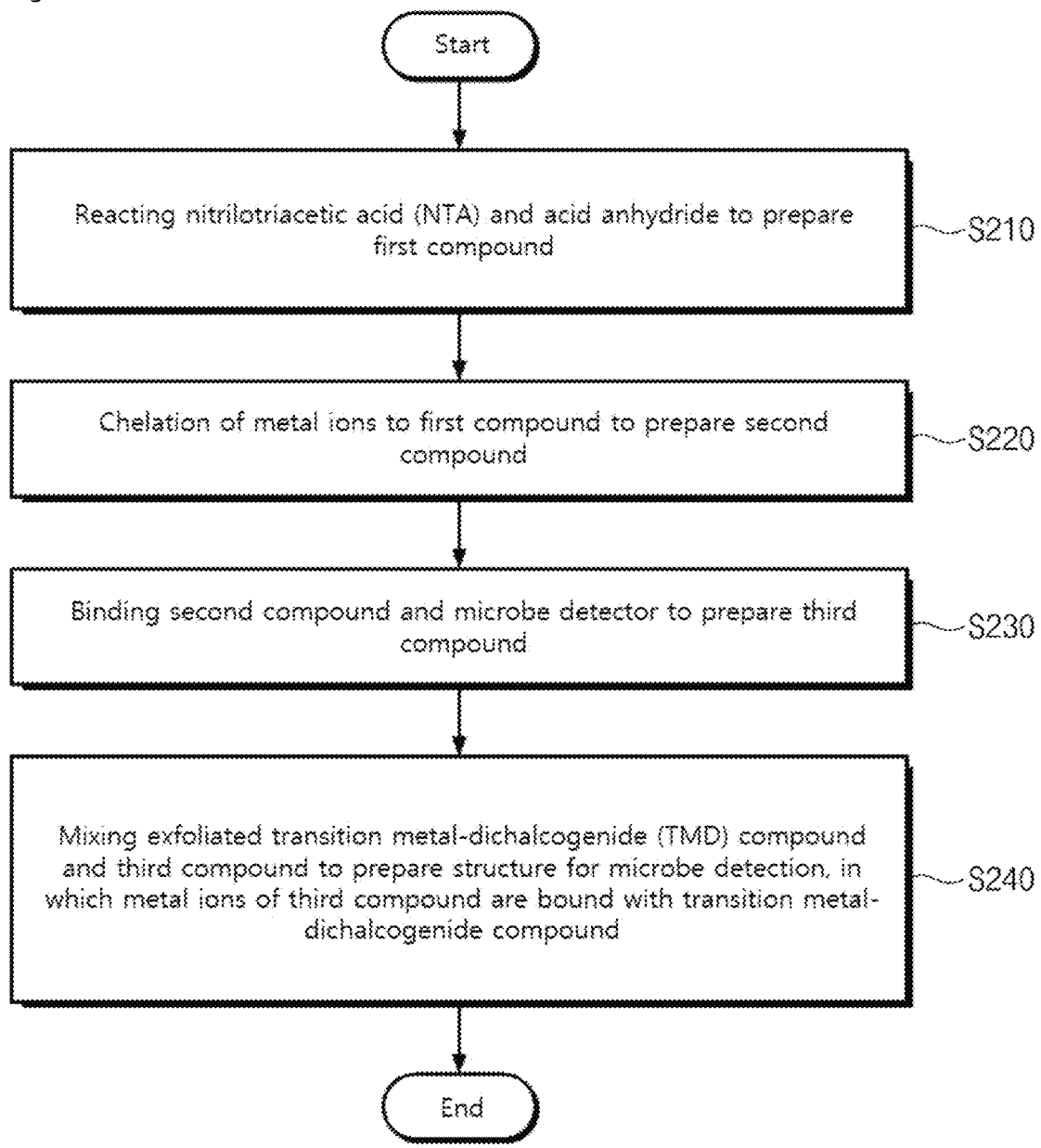

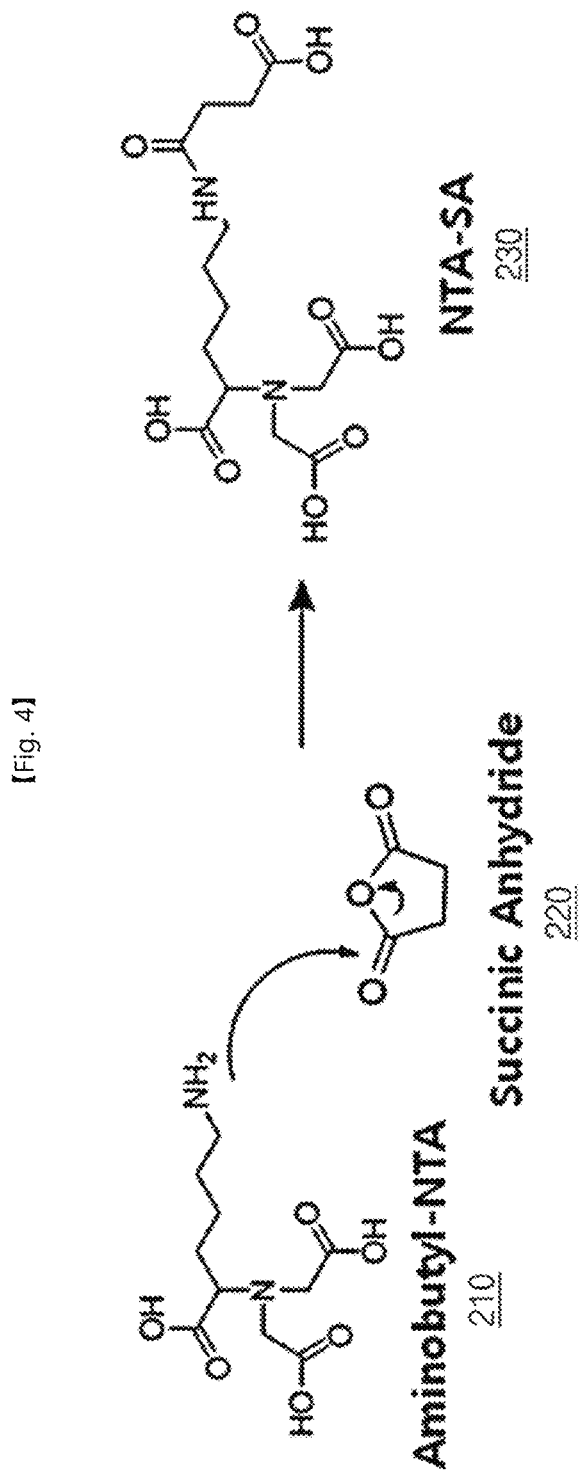

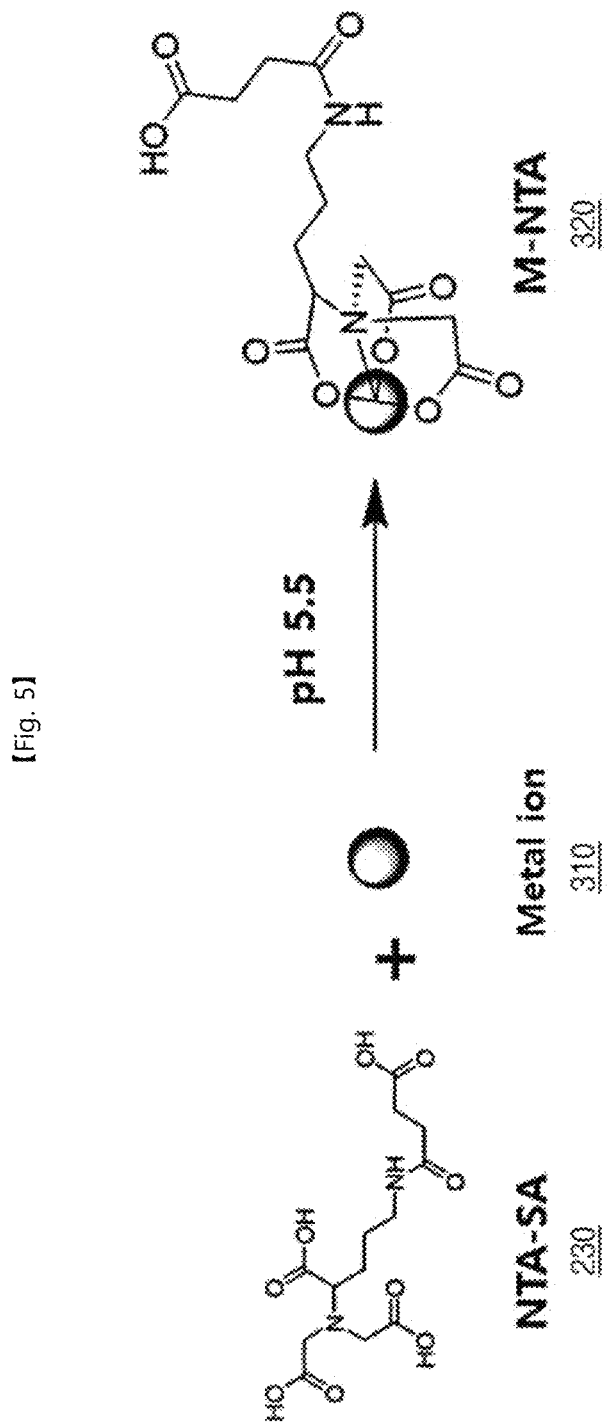

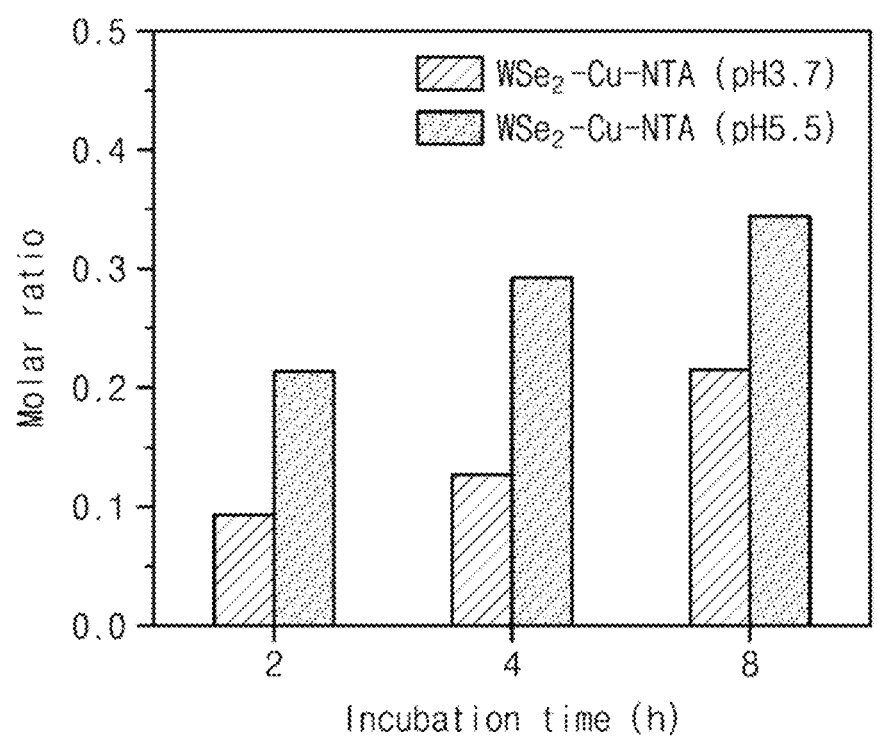
[Fig. 6]

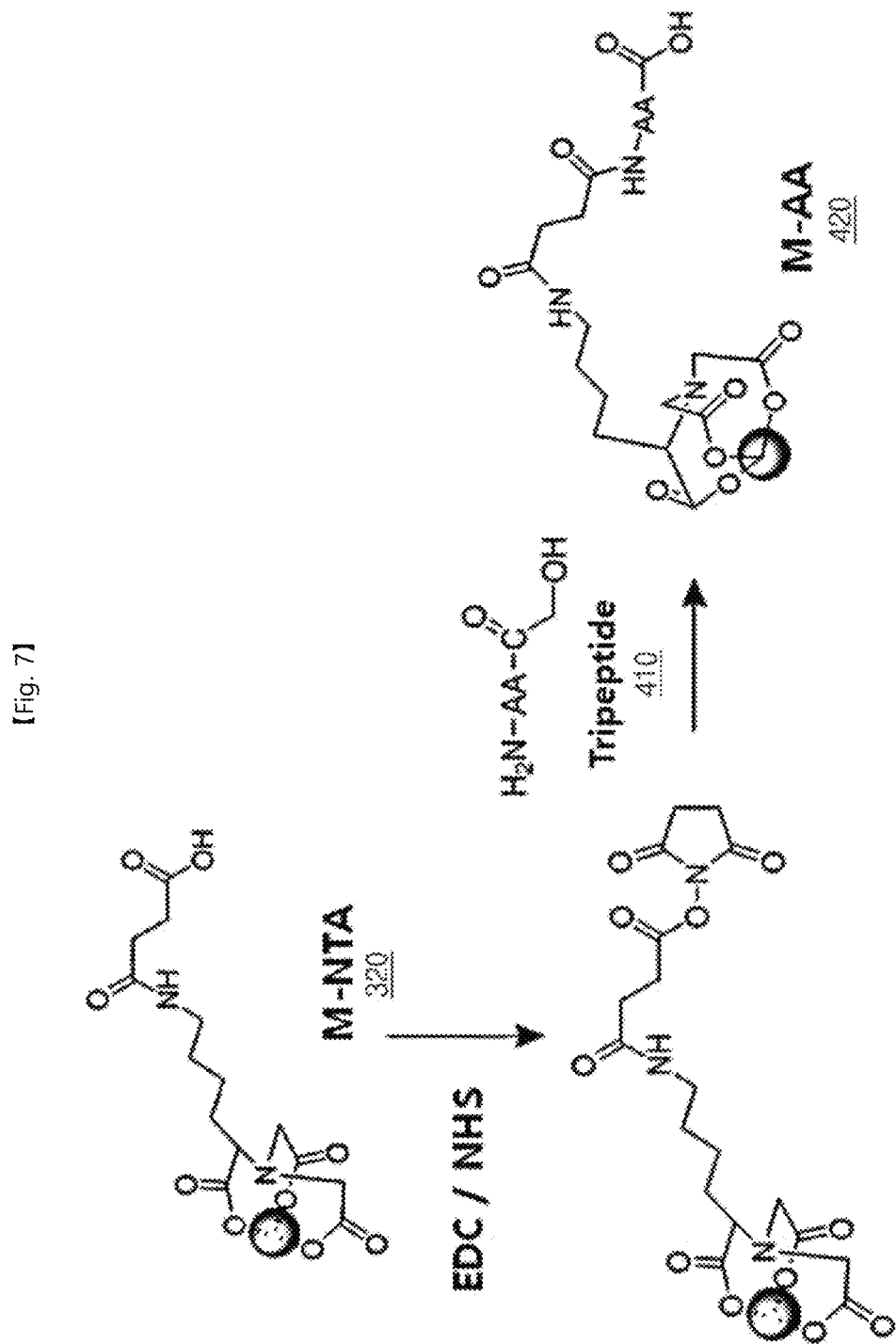

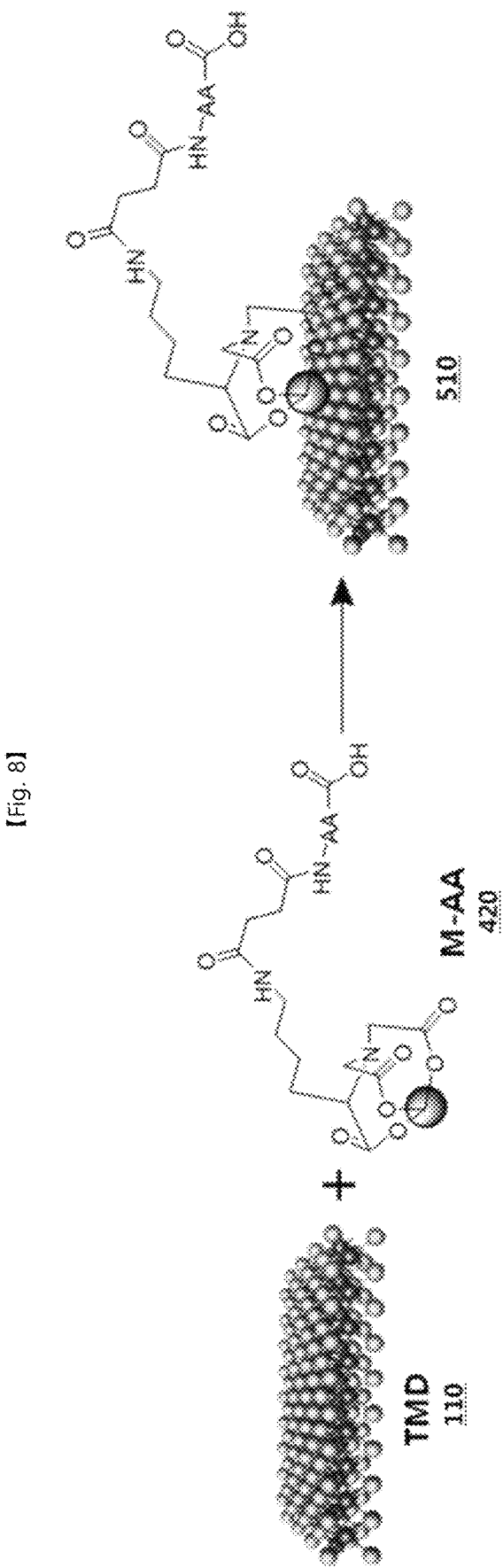
[Fig. 8]

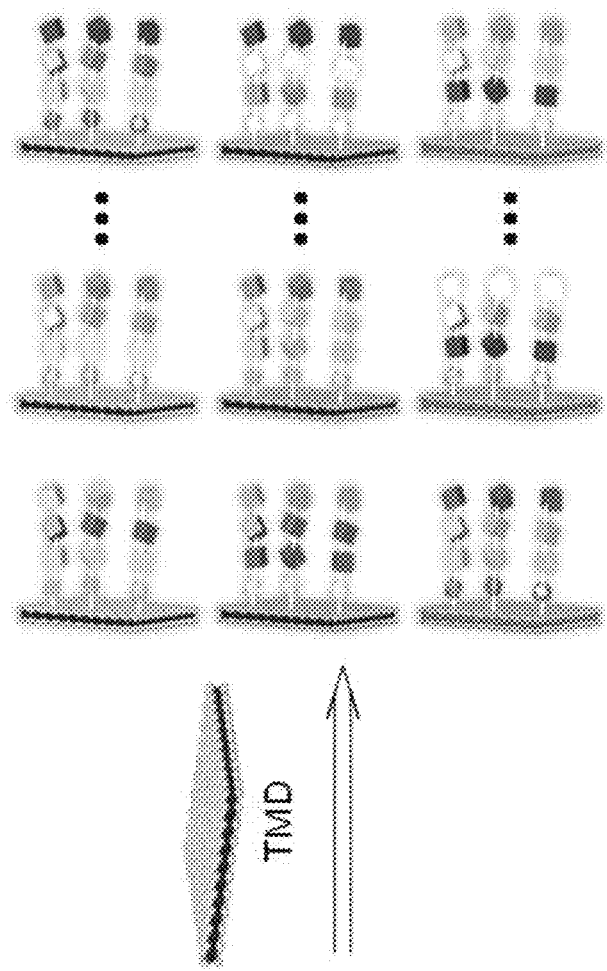

[Fig. 10]
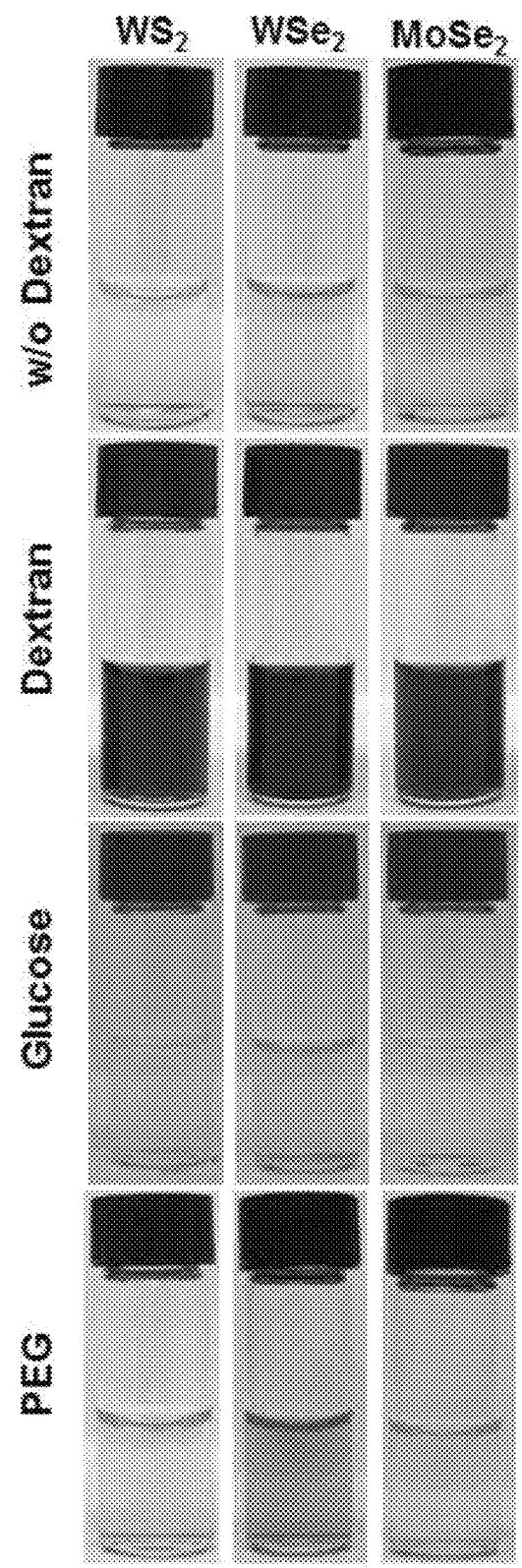

[Fig. 11]
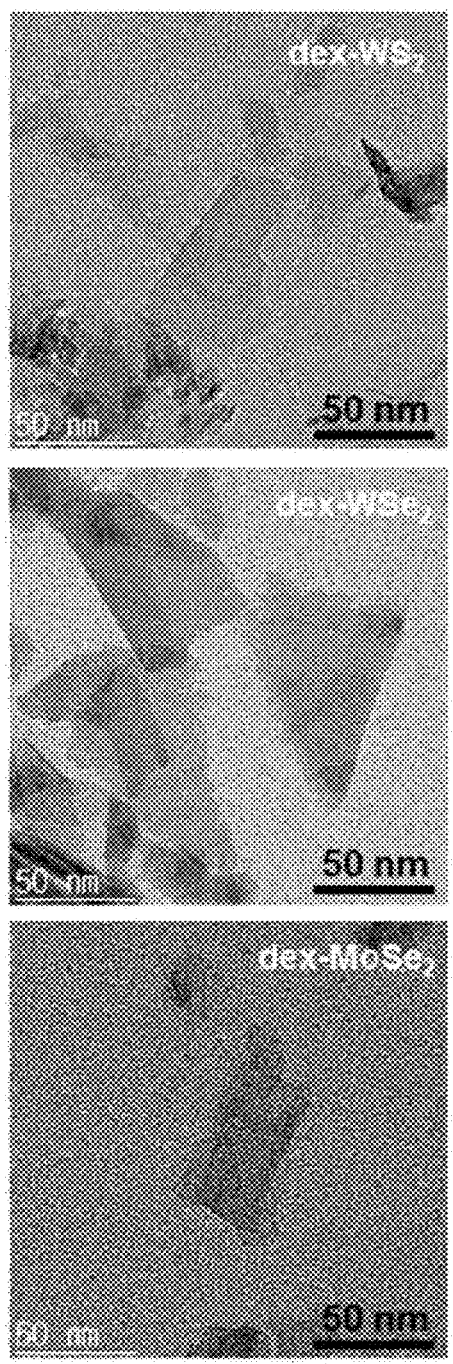

[Fig. 12]
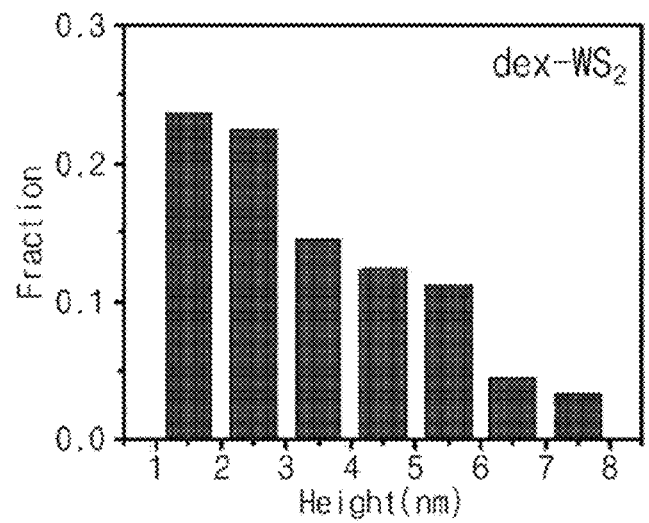
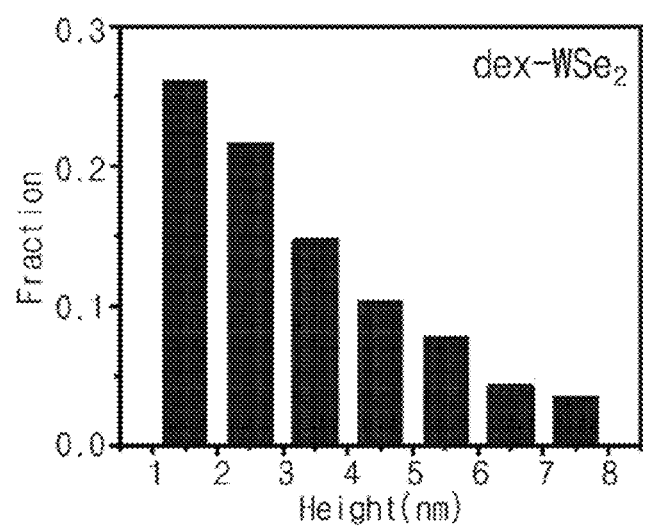
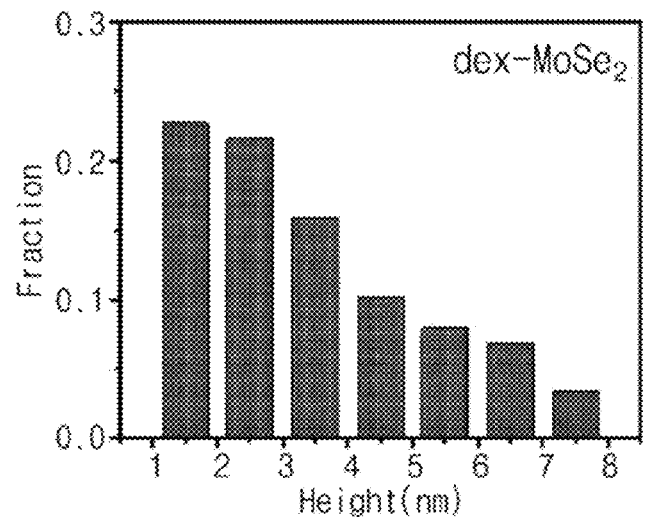

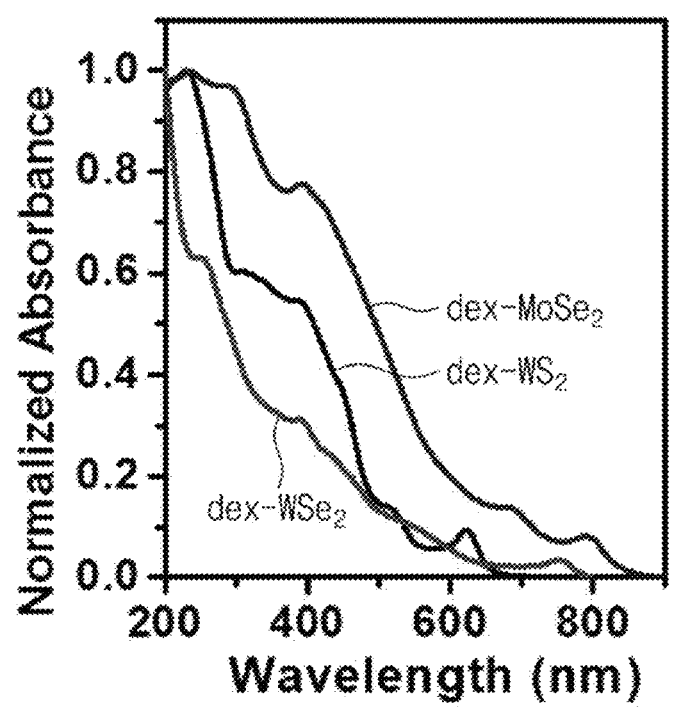
[Fig. 13]

[Fig. 14]
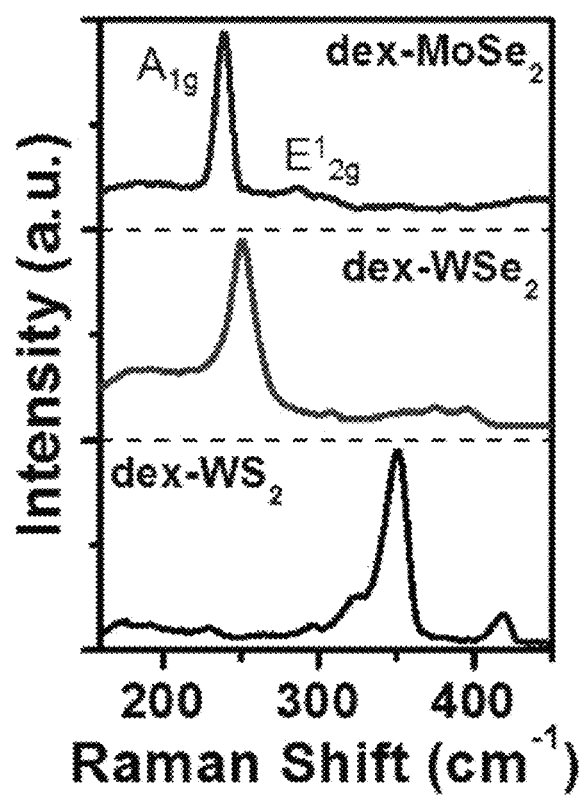

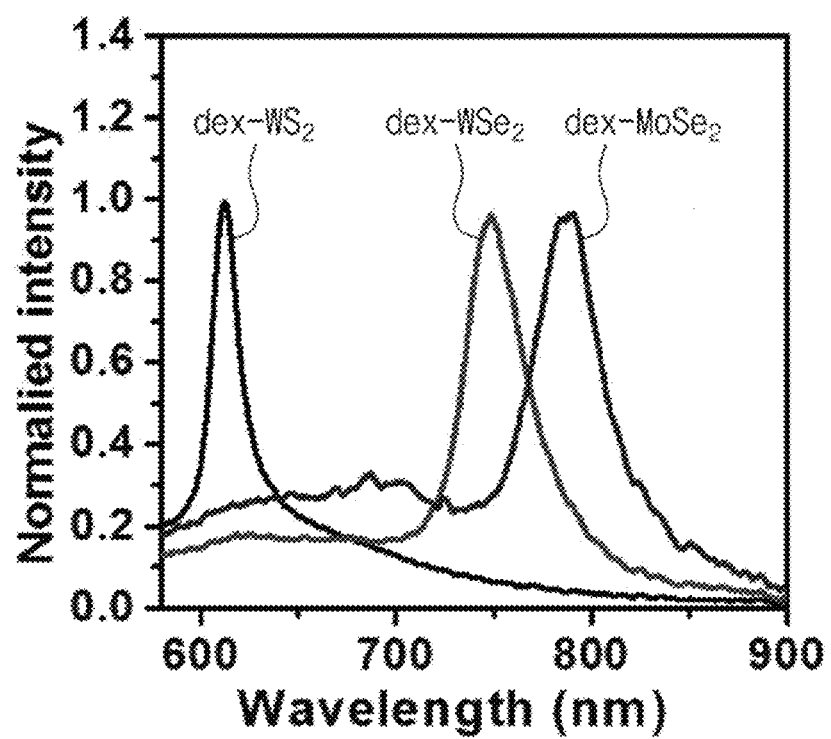
[Fig. 15]

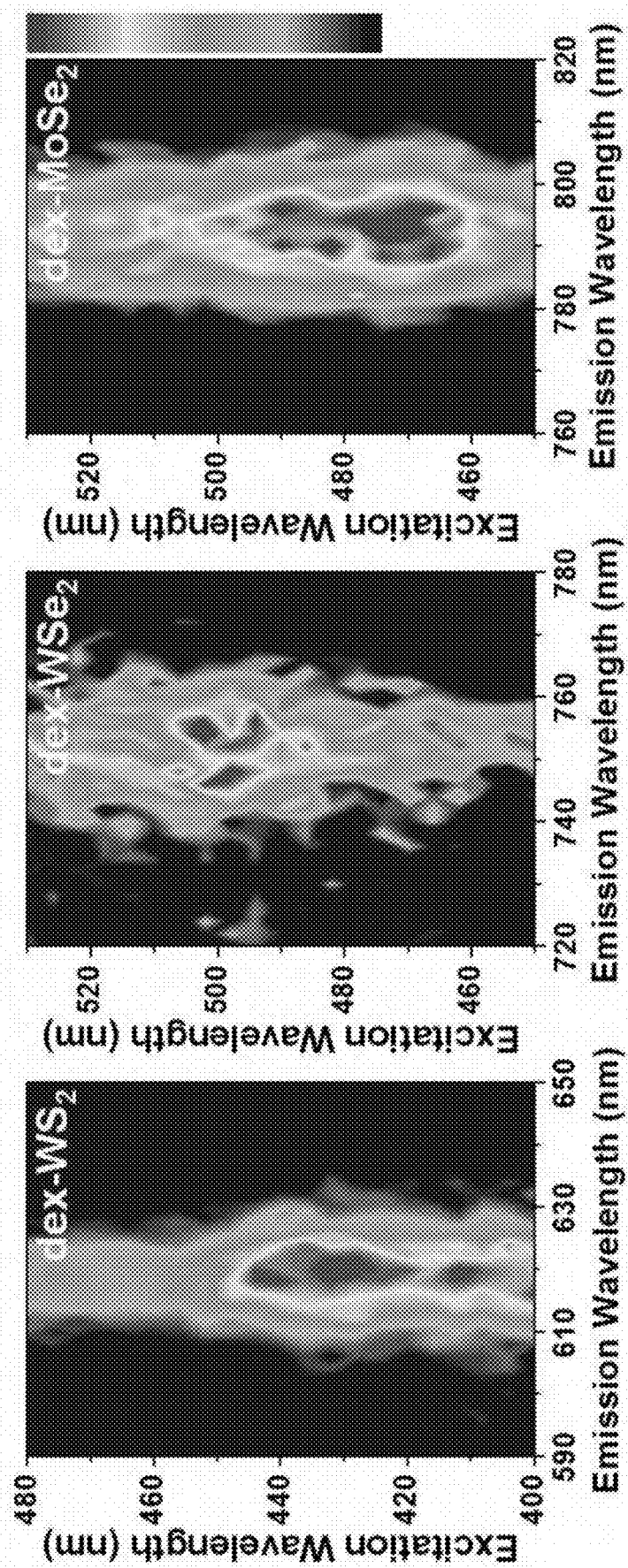
[Fig. 16]

[Fig. 17]
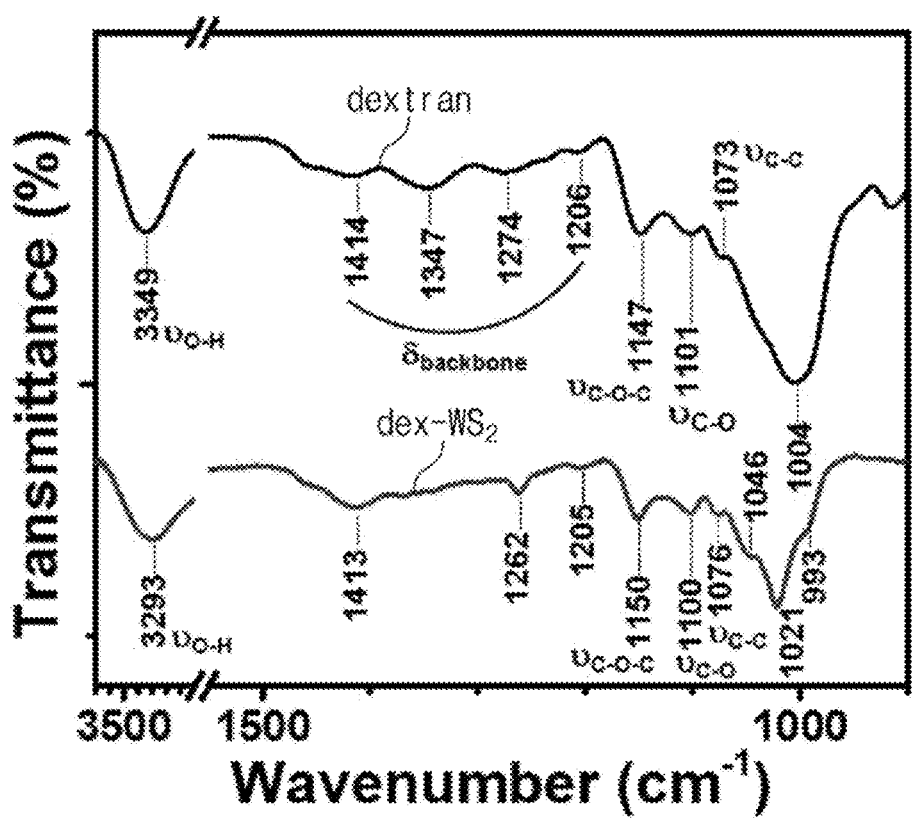

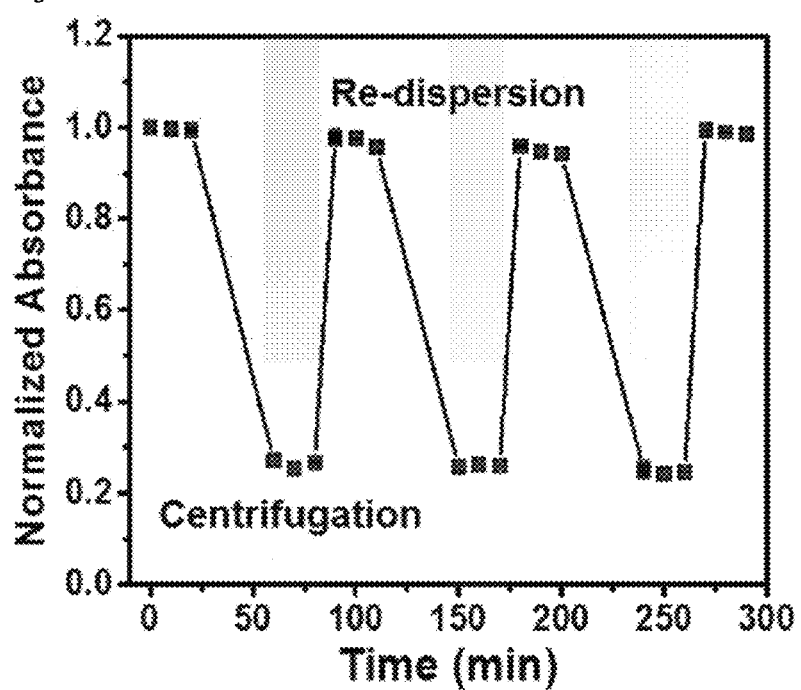
[Fig. 18]

[Fig. 19]
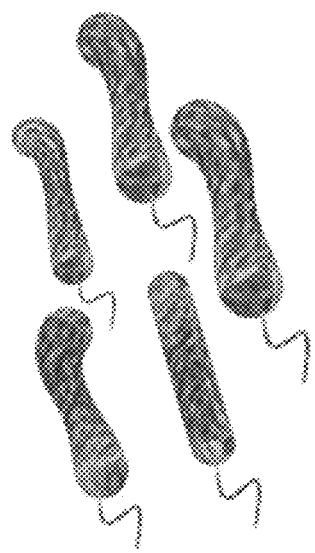
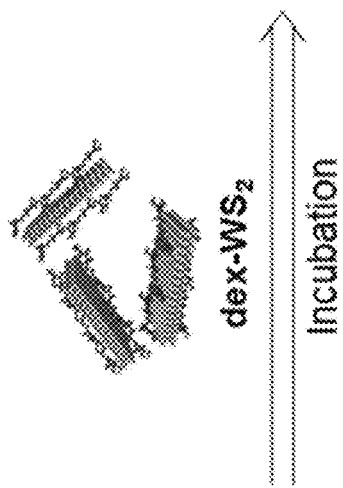
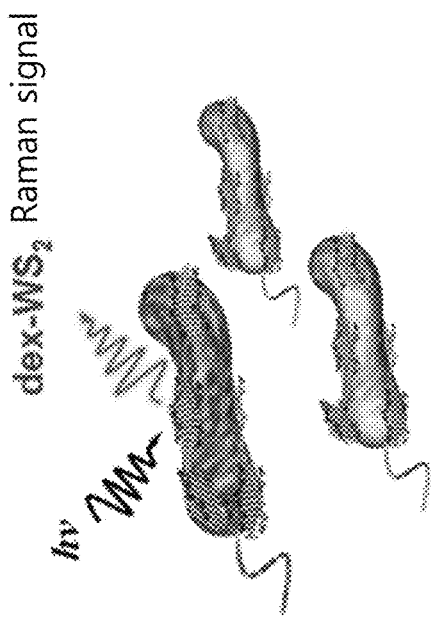

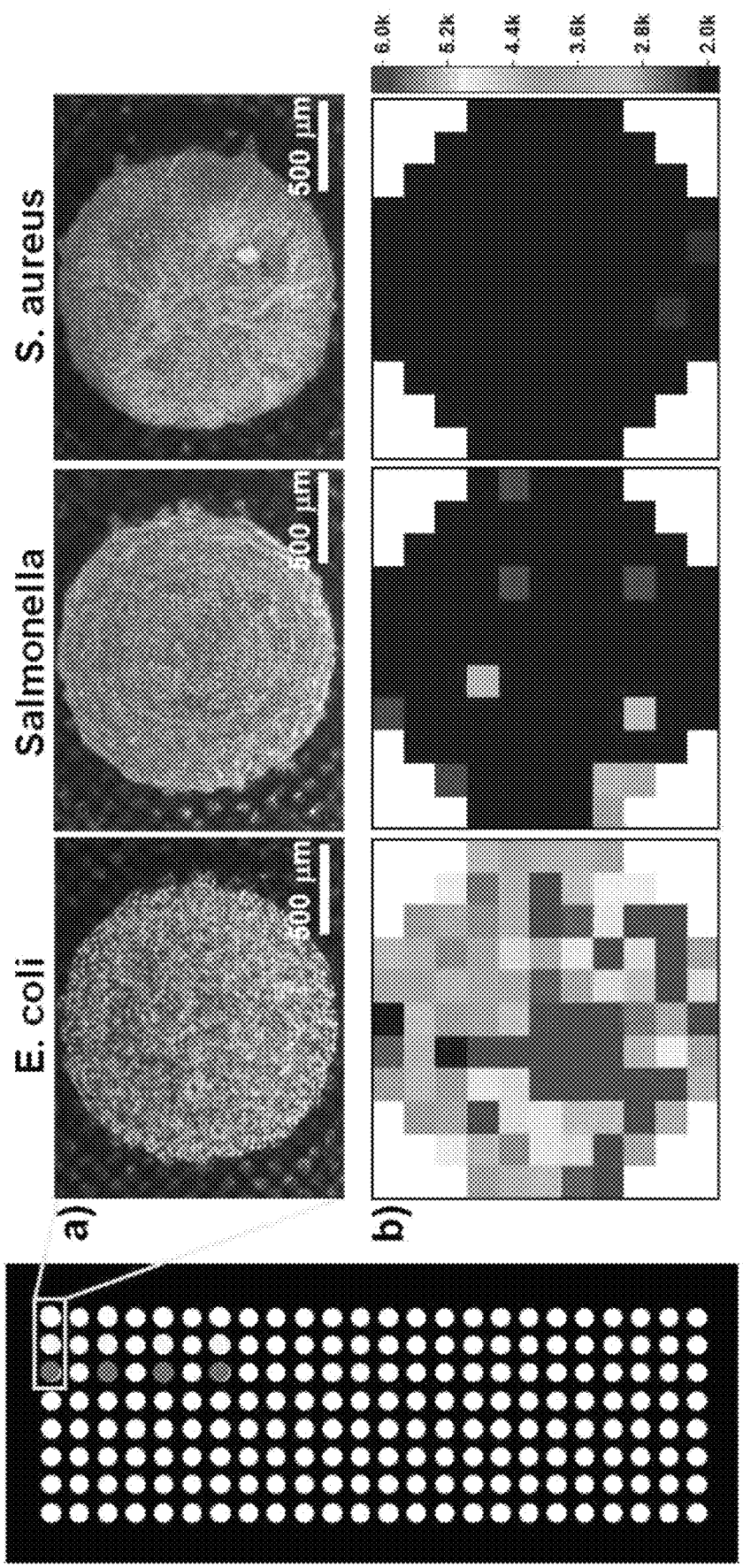
[Fig. 20]

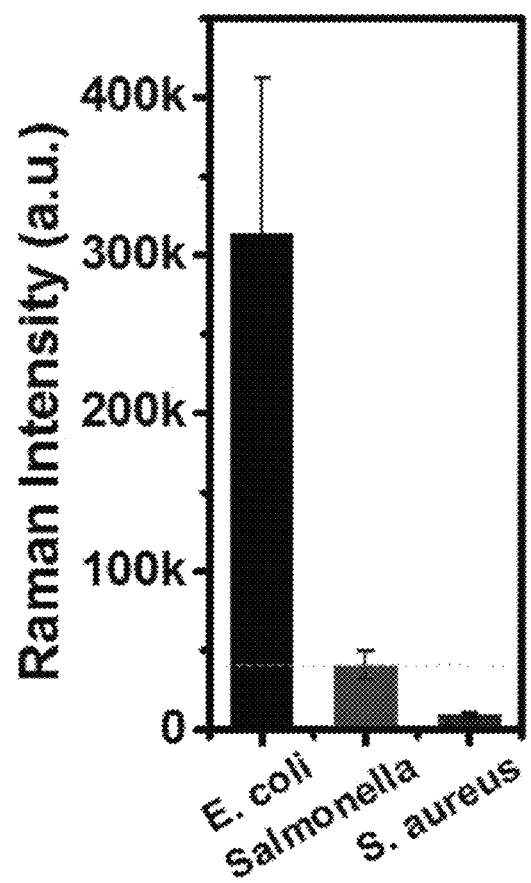
[Fig. 21]

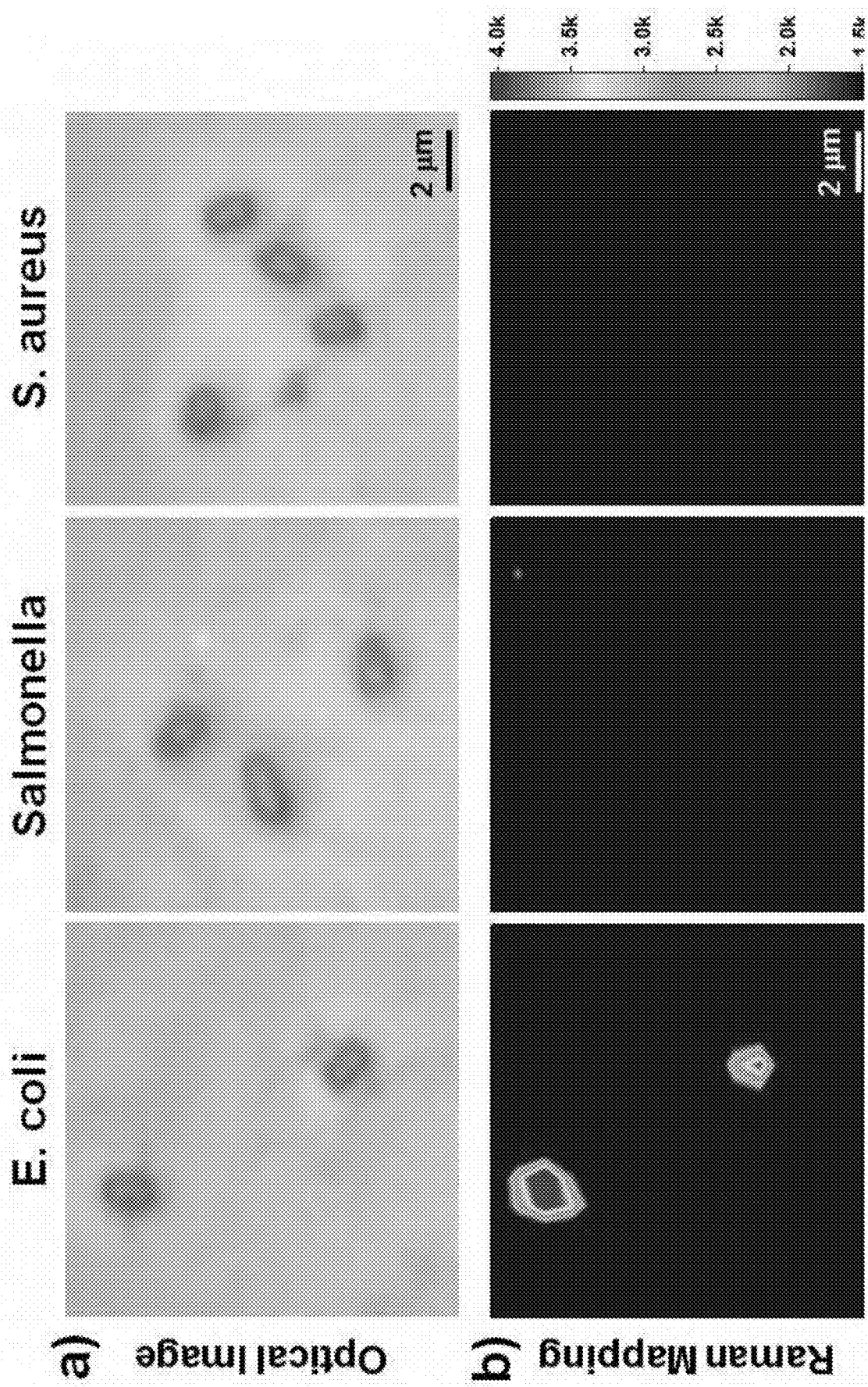
[Fig. 22]

[Fig. 23]
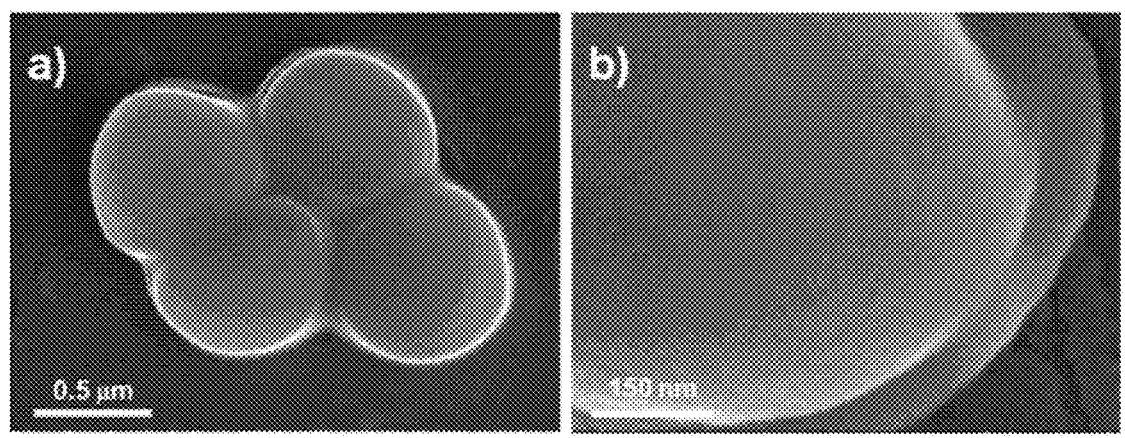

[Fig. 24]
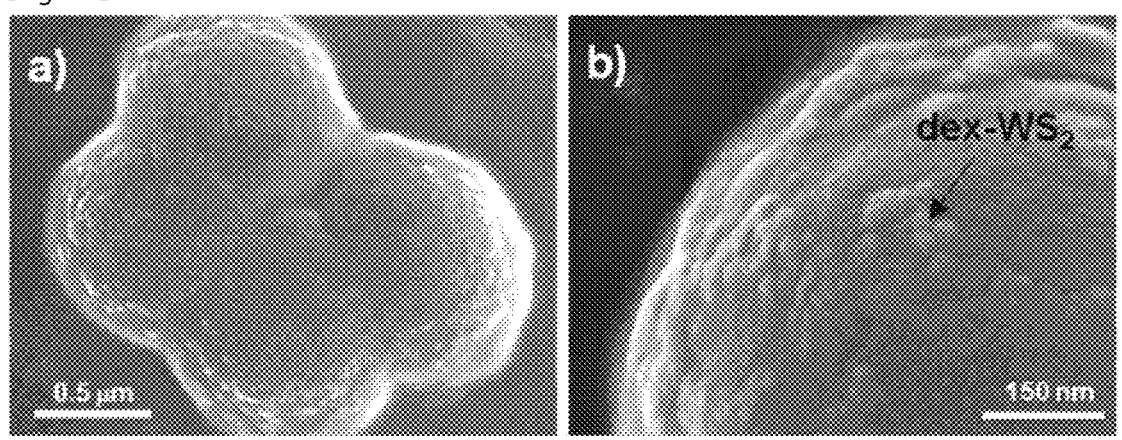

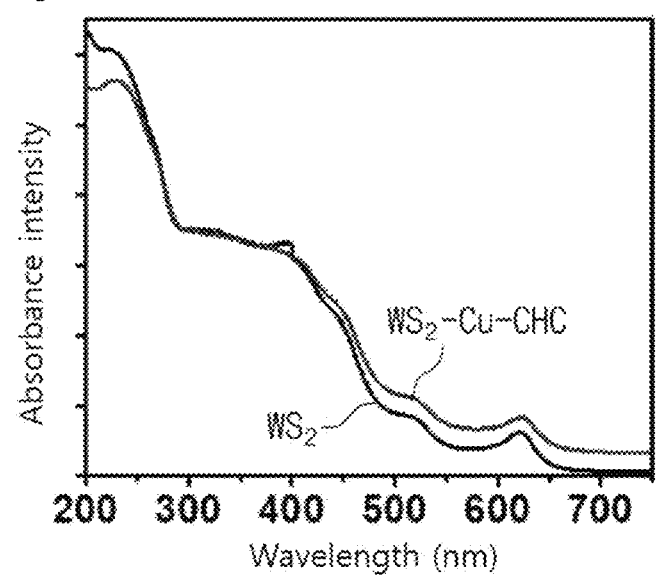
[Fig. 25]

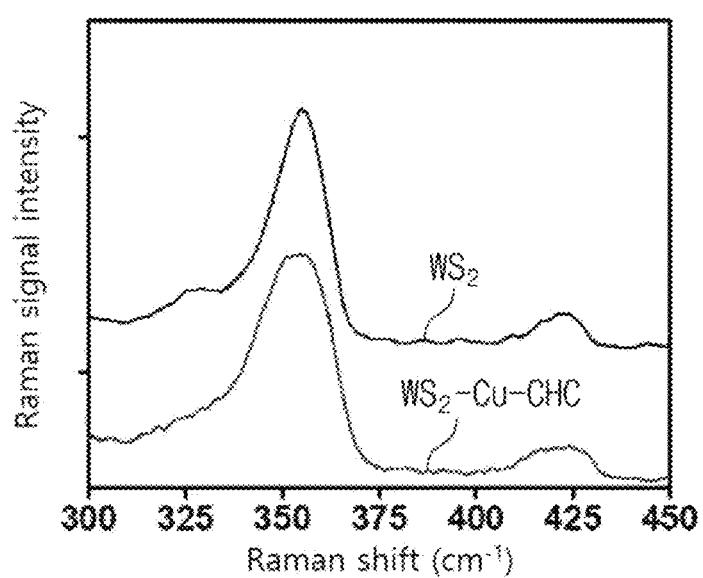
[Fig. 26]

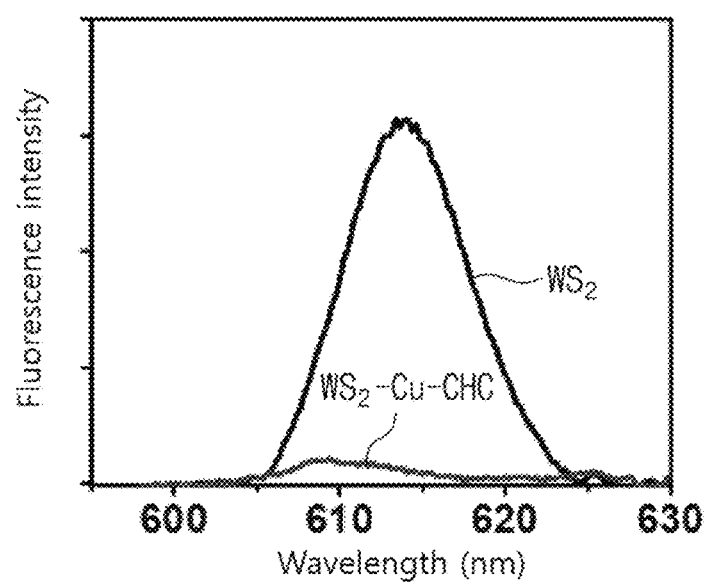
[Fig. 27]

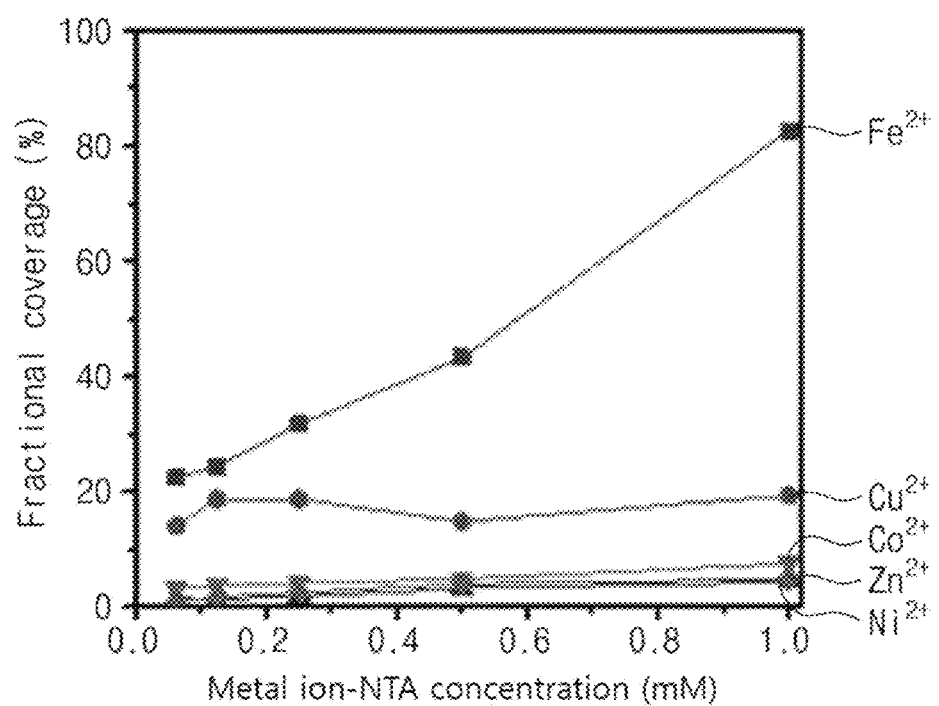
[Fig. 28]

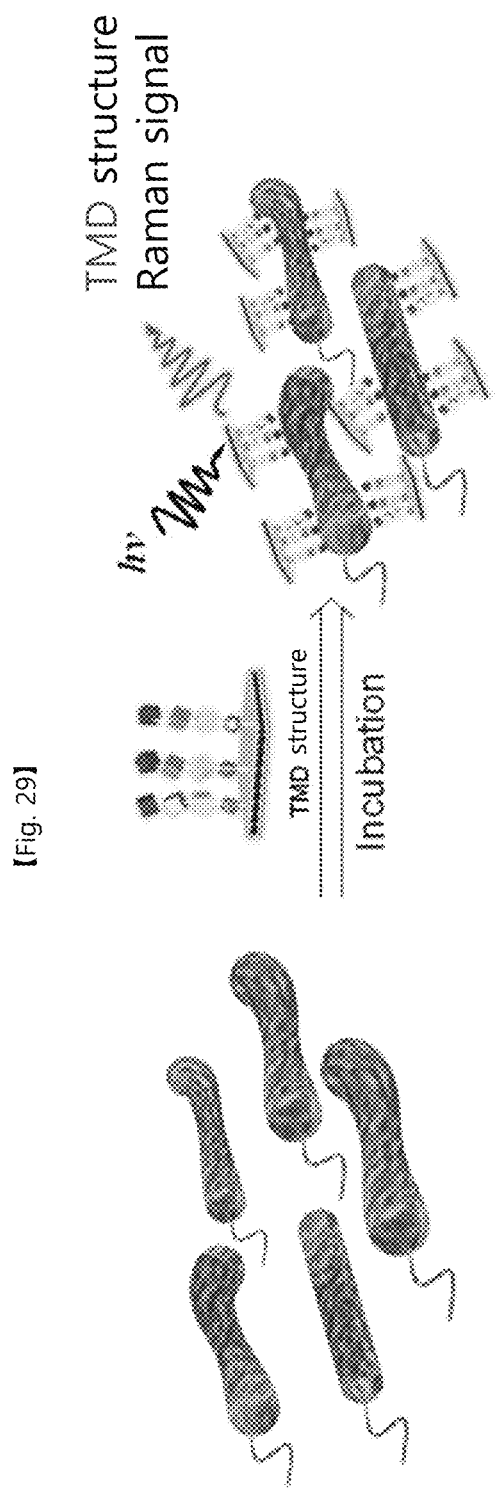
[Fig. 29]

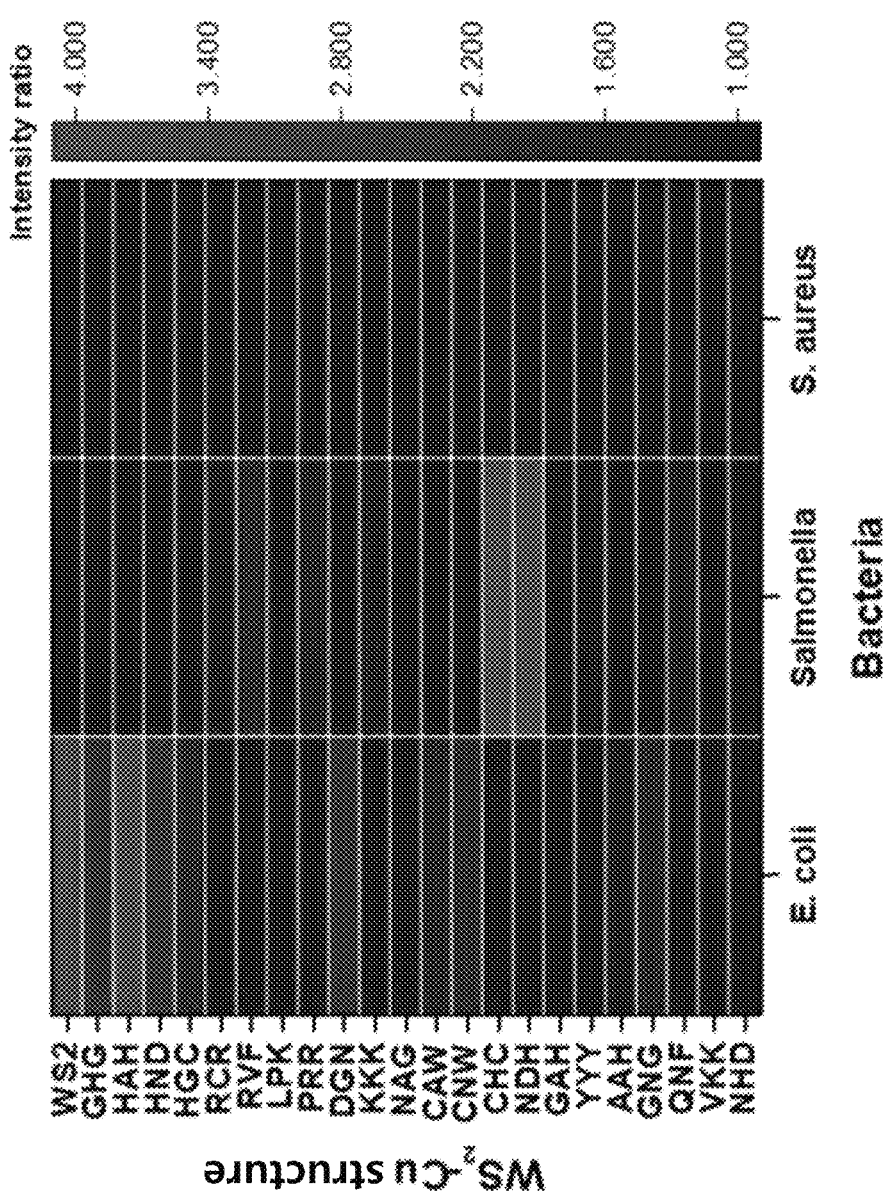
[Fig. 30]

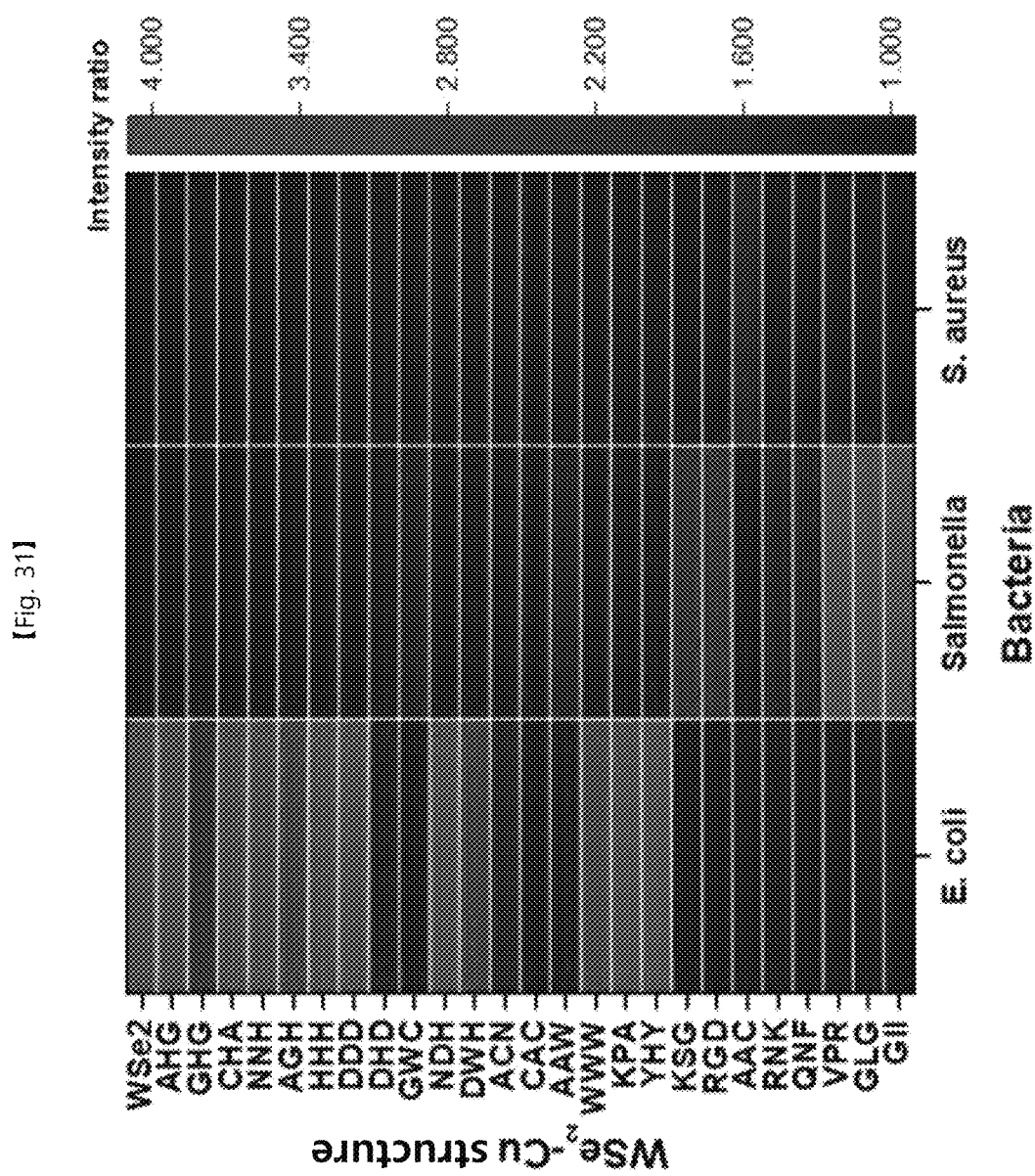
[Fig. 31]

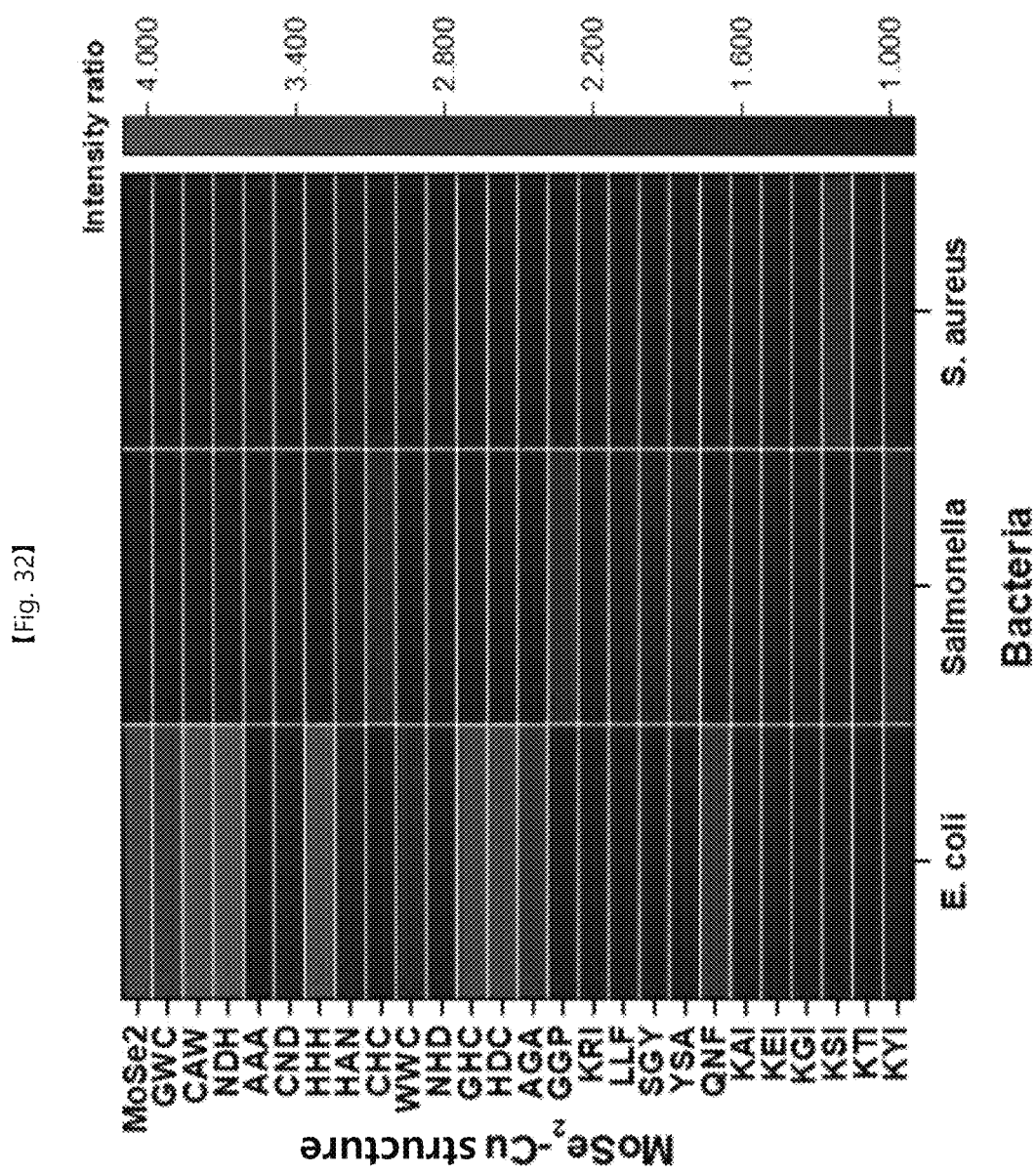
[Fig. 32]

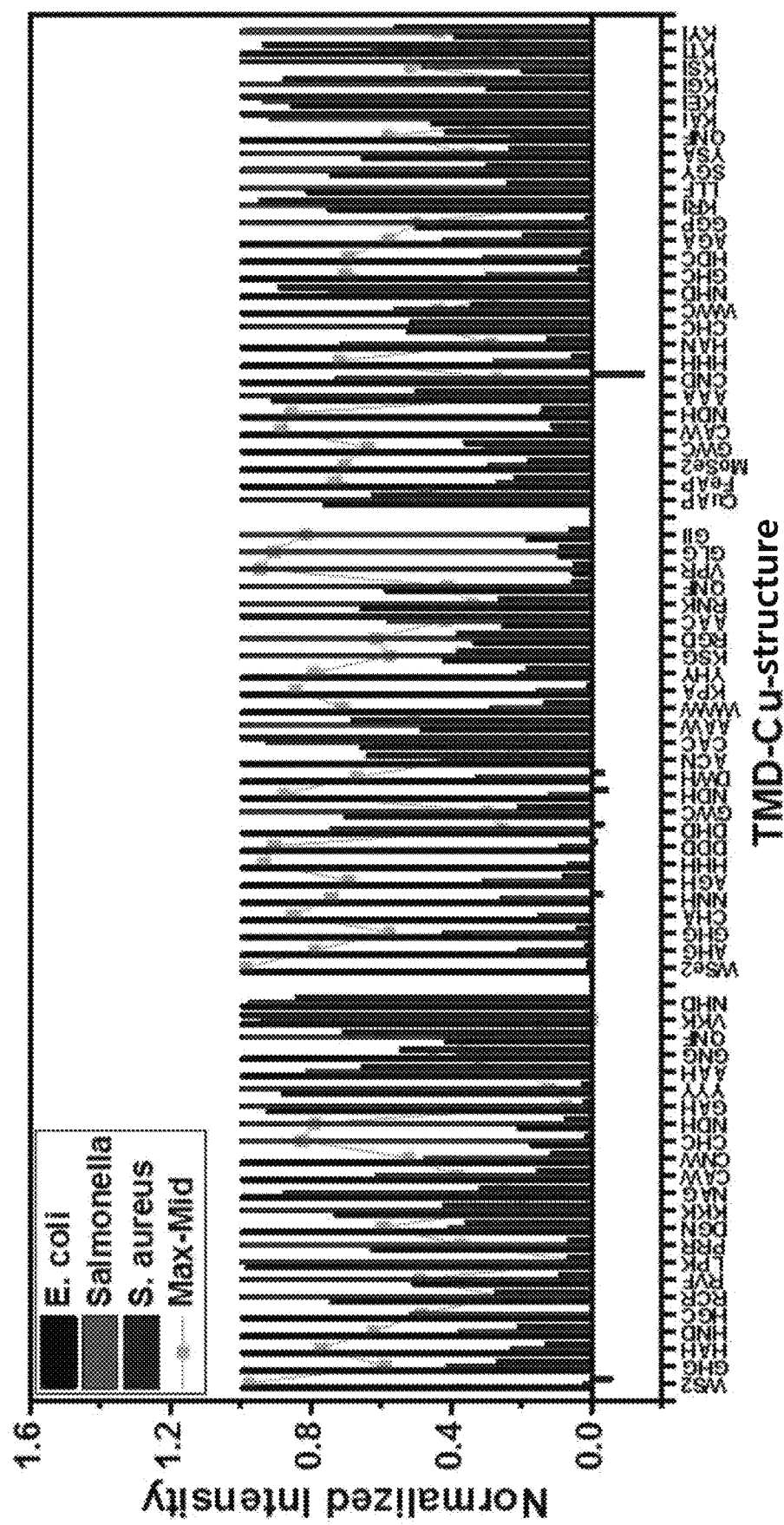
[Fig. 33]

STRUCTURE FOR MICROBE DETECTION, MANUFACTURING METHOD THEREFOR, AND MICROBE DETECTION METHOD USING SAME STRUCTURE FOR MICROBE DETECTION

TECHNICAL FIELD

The present invention relates to a structure for microbe detection, a manufacturing method therefor, and a microbe detection method using the same structure for microbe detection and, more particularly, to a structure for microbe detection, containing metal ions bound to an exfoliated transition metal-dichalcogenide (TMD) compound, nitrilotriacetic acid (NTA) bound with the metal ions, and a microbe detector bound to the nitrilotriacetic acid, a manufacturing method therefor, and a microbe detection method using the same structure for microbe detection.

BACKGROUND ART

As a conventional method for detecting microbes and bacteria, a selective medium method has been used. The selective medium method is performed by proliferating specific microbes and bacteria by using a specific medium capable of selectively culturing the specific microbes and bacteria, selecting an object to be analyzed from the proliferated specific microbes and bacteria, and analyzing the object. However, the selective medium method has a disadvantage in that a process of detecting the microbes and bacteria is complicated and takes a long time.

Accordingly, a polymerase chain reaction (PCR) method, which compensates for the disadvantage of the selective medium method, has been proposed. The PCR method is a detection method which is performed by inducing a strong signal through amplification of a gene extracted from a colony of the microbes and bacteria. For example, Korean Patent Publication No. KR 20140071968 A discloses a method for detecting a microbial infection in a subject by PCR, the method including: adding a plurality of fusion probes composed of a 5' terminal region having a non-bacterial DNA sequence and a 3' terminal region having a sequence complementary to a part of the target microbial DNA into a sample of a subject; hybridizing the fusion probe to a microbial DNA in the sample; removing any unbound 3' terminal region of the microbial DNA and the non-hybridized fusion probe; extending the 3' terminal of the fusion probe and the microbial DNA to form a template with a double-stranded primer extended; amplifying the primer-extended template by performing a PCR method using a primer set including one or more forward primers having a non-bacterial sequence complementary to the non-bacterial sequence of the fusion probe; and analyzing the amplified PCR product to confirm the presence or absence of the microbes.

However, the PCR method has a problem in that it is difficult to secure a PCR primer, and a non-specific DNA is amplified due to a PCR fragment bias phenomenon, thereby causing a false positive determination.

Accordingly, an antibody-based immunoassay method, which compensates for the problem of the PCR method, has been proposed. The antibody-based immunoassay method is a method for analyzing the microbes and bacteria by using an antibody that acts as an antigen. However, the antibody-based immunoassay method has a disadvantage in that an antibody capable of recognizing a target antigen is very expensive and sensitive to the surrounding environment.

Accordingly, there is a need for developing technique with regard to a method for accurately detecting the microbes and bacteria at a low cost within a short time.

DISCLOSURE

Technical Problem

One technical object of the present invention is to provide a method for detecting microbes, which is accurately performed with a short time at a low cost.

Another technical object of the present invention is to provide a structure for microbe detection, including metal ions bound to an exfoliated transition metal-dichalcogenide (TMD) compound, nitrilotriacetic acid (NTA) bound with the metal ions and a microbe detector bound to the nitrilotriacetic acid.

Still another technical object of the present invention is to provide a structure for microbe detection including fluorescent and Raman scattering properties.

Still another technical object of the present invention is to provide a method for detecting microbes, in which fluorescent and Raman scattering properties are shown as a microbe detection signal, by using a structure for microbe detection including the fluorescent and Raman scattering properties.

Still another technical object of the present invention is to provide a method for detecting microbes, which selectively detects a specific microbe.

Still another technical object of the present invention is to provide a structure for bacterial detection including a polysaccharide polymer bound to an exfoliated transition metal-dichalcogenide compound.

Still another technical object of the present invention is to provide a structure for bacterial detection including fluorescent and Raman scattering properties.

Still another technical object of the present invention is to provide a method for detecting bacteria, in which fluorescent and Raman scattering properties are shown as a bacterial detection signal, by using a structure for bacterial detection including the fluorescent and Raman scattering properties.

Still another technical object of the present invention is to provide a method for detecting microbes, which selectively detects specific bacteria.

The technical objects of the present application are not limited to the above.

Technical Solution

To solve the technical objects as described above, the present invention provides a method for preparing a structure for microbe detection.

According to one embodiment, the method for preparing a structure for microbe detection may include: reacting nitrilotriacetic acid (NTA) and an acid anhydride to prepare a first compound; chelation of metal ions to the first compound to prepare a second compound; binding the second compound and a microbe detector to prepare a third compound; and mixing an exfoliated transition metal-dichalcogenide (TMD) compound and the third compound to prepare a structure for microbe detection, in which the metal ions of the third compound are bound with the transition metal-dichalcogenide compound.

According to one embodiment, the preparing of the first compound may include: dissolving the nitrilotriacetic acid in a solvent; adding and stirring the acid anhydride and a non-nucleophilic basic material into the solvent in which the nitrilotriacetic acid is dissolved, so as to prepare a mixed solution containing a preliminary first compound; adding an excessive amount of ester into the mixed solution to precipitate the preliminary first compound of the mixed solution; and washing and freeze-drying the precipitated preliminary first compound to prepare the first compound.

According to one embodiment, the preparing of the second compound may include dissolving the first compound in a solvent and adding the metal ions into the resulting solution.

According to one embodiment, the preparing of the second compound may be performed at pH in a range of more than 3.7 and less than 6.0.

According to one embodiment, the preparing of the third compound may include adding a cross-linking agent including carbodiimide into the second compound; and adding and stirring the microbe detector into the second compound to which the cross-linking agent is added.

According to one embodiment, the adding of the cross-linking agent into the second compound may include adding an activation material of the cross-linking agent in addition to the cross-linking agent.

According to one embodiment, the microbe detector may include at least one of biomolecules including peptide, DNA or RNA.

To solve the technical objects as described above, there may be provided a structure for microbe detection.

According to one embodiment, the structure for microbe detection may include an exfoliated transition metal-dichalcogenide compound, and a compound for microbe detection bound with the transition metal-dichalcogenide compound.

According to one embodiment, the compound for microbe detection may include metal ions bound to the transition metal-dichalcogenide compound, nitrilotriacetic acid bound with the metal ions, and a microbe detector bound to the nitrilotriacetic acid.

To solve the technical objects as described above, there may be provided a method for detecting microbes.

According to one embodiment, the method for detecting microbes may include binding a microbe including at least one of *Escherichia coli, Staphylococcus aureus* or *Salmonella* to the microbe detector of the structure for microbe detection.

To solve the technical objects as described above, there may be provided a method for detecting bacteria.

According to one embodiment, the method for detecting bacteria may include: providing a polysaccharide polymer containing a hydroxyl group (—OH); mixing the polysaccharide polymer and a transition metal-dichalcogenide compound in a solvent to prepare a structure for bacterial detection in which the transition metal-dichalcogenide compound is exfoliated by the hydroxyl group of the polysaccharide polymer and the polysaccharide polymer and the exfoliated transition metal-dichalcogenide compound are bound; and binding an object to be detected to the polysaccharide polymer of the structure for bacterial detection.

According to one embodiment, the object to be detected may include *Escherichia coli*.

Advantageous Effects

According to Example 1 of the present invention, there may be provided a method for detecting bacteria, the method including: providing a polysaccharide polymer containing a hydroxyl group (—OH); mixing the polysaccharide polymer and a transition metal-dichalcogenide compound in a solvent to prepare a structure for bacterial detection in which the transition metal-dichalcogenide compound is exfoliated by the hydroxyl group of the polysaccharide polymer and the polysaccharide polymer and the exfoliated transition metal-dichalcogenide compound are bound; and binding an object to the detected to the polysaccharide polymer of the structure for bacterial detection.

According to Example 1 of the present invention, the structure for bacterial detection may include the exfoliated transition metal-dichalcogenide compound and thus sense Raman scattering properties as a signal, thereby providing an effect of easily detecting bacteria. In addition, according to Example 1 of the present invention, the structure for microbe detection may include the polysaccharide polymer, thereby providing an effect of selectively detecting a specific microbe.

According to Example 2 of the present invention, there may be provided a method for preparing a structure for microbe detection, the method including: reacting nitrilotriacetic acid (NTA) and an acid anhydride to prepare a first compound: chelation of metal ions to the first compound to prepare a second compound; binding the second compound and a microbe detector to prepare a third compound; and mixing an exfoliated transition metal-dichalcogenide (TMD) compound and the third compound to prepare a structure for microbe detection, in which the metal ions of the third compound are bound with the transition metal-dichalcogenide compound.

According to Example 2 of the present invention, the structure for microbe detection may include the exfoliated transition metal-dichalcogenide compound and thus sense Raman scattering properties as a signal, thereby providing an effect of easily detecting microbes. In addition, according to Example 2 of the present invention, the structure for microbe detection may include the microbe detector, thereby providing an effect of selectively detecting a specific microbe.

DESCRIPTION OF DRAWINGS

FIG. 1 is a flowchart for explaining a method for detecting bacteria according to Example 1 of the present invention.

FIG. 2 is a view for explaining a method for preparing a structure for bacterial detection according to Example 1 of the present invention.

FIG. 3 is a flow chart for explaining a method for preparing a structure for microbe detection according to Example 2 of the present invention.

FIG. 4 is a view for explaining a method for preparing a first compound according to Example 2 of the present invention.

FIG. 5 is a view for explaining a method for preparing a second compound according to Example 2 of the present invention.

FIG. 6 is a view for explaining a change in properties depending on pH of a second compound according to Example 2 of the present invention.

FIG. 7 is a view for explaining a method for preparing a third compound according to Example 2 of the present invention.

FIG. 8 is a view for explaining a method for preparing a structure for microbe detection according to Example 2 of the present invention.

FIG. 9 is a view for explaining a structure for microbe detection according to Example 2 of the present invention.

FIG. 10 is a view showing pictures for explaining a method for preparing a structure for bacterial detection according to Experimental Examples 1-1 to 1-3 of the present invention.

FIG. 11 is a view showing transmission electron microscope (TEM) pictures of a structure for bacterial detection according to Experimental Examples 1-1 to 1-3 of the present invention.

FIG. 12 is a view showing results of measuring a thickness of a structure for bacterial detection according to Experimental Examples 1-1 to 1-3 of the present invention.

FIG. 13 is a graph showing an UV-Vis absorbance of a structure for bacterial detection according to Experimental Examples 1-1 to 1-3 of the present invention.

FIG. 14 is a graph showing Raman scattering of a structure for bacterial detection according to Experimental Examples 1-1 to 1-3 of the present invention.

FIG. 15 is a graph showing fluorescence spectra of structures for bacterial detection according to Experimental Examples 1-1 to 1-3 of the present invention.

FIG. 16 is an image showing two-dimensional fluorescence signal mapping of a structure for bacterial detection according to Experimental Examples 1-1 to 1-3 of the present invention.

FIG. 17 is a view showing FT-IR spectra of structures for bacterial detection according to Experimental Example 1-1 of the present invention.

FIG. 18 is a graph showing a measured absorbance of a structure for bacterial detection according to Experimental Example 1-1 of the present invention.

FIG. 19 is a view for explaining a method for detecting bacteria by using a structure for bacterial detection according to Example 1 of the present invention.

FIG. 20 in (a) is an optical image showing bacteria detected by using a structure for bacterial detection according to Example 1-1 of the present invention. FIG. 20 in (b) is a view showing mapping of bacteria using Raman analysis, which are detected by using a structure for bacterial detection according to Experimental Example 1-1 of the present invention.

FIG. 21 is a graph showing Raman signal intensity of bacteria detected by using a structure for bacterial detection according to Experimental Example 1-1 of the present invention.

FIG. 22 in (a) is an optical image showing *Escherichia coli, Salmonella*, and *Staphylococcus aureus*. FIG. 22 in (b) is a view showing Raman mapping of bacteria detected by using a structure for bacterial detection according to Experimental Example 1-1 of the present invention.

FIG. 23 in (a) and (b) are views showing SEM pictures of *Escherichia coli*.

FIG. 24 in (a) and (b) are views showing SEM pictures of *Escherichia coli* detected by using a structure for bacterial detection according to Experimental Example 1-1 of the present invention.

FIG. 25 is a graph showing an UV-V is absorbance of a structure for microbe detection according to Experimental Example 2-1 of the present invention.

FIG. 26 is a graph showing Raman scattering of a structure for microbe detection according to Experimental Example 2-1 of the present invention.

FIG. 27 is a graph showing fluorescence spectra of structures for microbe detection according to Experimental Example 2-1 of the present invention.

FIG. 28 is a graph for explaining an amount of introduced various metal ions bound to a structure for microbe detection in a method for preparing a structure for microbe detection according to Example 2 of the present invention.

FIG. 29 is a view for explaining a method for detecting microbes by using a structure for microbe detection according to Example 2 of the present invention.

FIG. 30 is a table showing two-dimensional mapping analysis of microbes detected by using a structure for microbe detection according to Experimental Example 2-1 of the present invention.

FIG. 31 is a table showing two-dimensional mapping analysis of microbes detected by using a structure for microbe detection according to Experimental Example 2-2 of the present invention.

FIG. 32 is a table showing two-dimensional mapping analysis of microbes detected by using a structure for microbe detection according to Experimental Example 2-3 of the present invention.

FIG. 33 is a graph showing results of detecting microbes by using a structure for microbe detection according to Example 2 of the present invention.

MODE FOR INVENTION

Hereinafter, preferred embodiments of the present invention will be described in detail with reference to the accompanying drawings. However, the technical idea of the present invention is not limited to the embodiments described herein and may be embodied in other forms. Rather, the embodiments introduced herein are provided so that the disclosed content may be thorough and complete, and the spirit of the present invention may be sufficiently conveyed to those skilled in the art.

When it is mentioned in the specification that one element is on another element, it means that the first element may be directly formed on the second element or a third element may be interposed between the first element and the second element. In addition, in the drawings, thicknesses of films and regions are exaggerated for effective description of technical content.

Further, in the various embodiments of the present invention, the terms such as first, second, and third are used to describe various elements, but the elements are not limited to the terms. These terms are only used to distinguish one component from another component. Accordingly, a first component referred in one embodiment may be referred to as a second component in another embodiment. Each embodiment described and illustrated herein also includes an embodiment complementary thereto. In addition, in the present specification, "and/or" is used to mean that at least one of the elements listed before and after is included.

In the specification, the terms of a singular form may include plural forms unless otherwise specified. In addition, terms such as "include" or "have" are intended to designate the presence of a characteristic, a number, a step, an element, a combination thereof, and shall not be construed to exclude any presence or possibility of one or more other characteristics, numbers, steps, elements, or combinations thereof.

Further, in the following description of the present invention, a detailed description of known functions and configurations incorporated herein will be omitted when it may make the subject matter of the present invention unnecessarily unclear.

Hereinafter, a method for preparing a structure for bacterial detection and a method for detecting bacteria according to Example 1 of the present invention will be described.

FIG. 1 is a flow chart for explaining a method for detecting bacteria according to Example 1 of the present invention, and FIG. 2 is a view for explaining a method for preparing a structure for microbe detection according to Example 1 of the present invention.

Referring to FIGS. 1 and 2, a polysaccharide polymer 120 containing a hydroxyl group (—OH) 121 may be provided (S110). According to Example 1 of the present invention, the polysaccharide polymer 120 may be dextran. The polysaccharide polymer 120 may contain a plurality of the hydroxyl groups 121. Accordingly, if the polysaccharide polymer 120 and a plurality of layered materials react to each other, a multivalent hydrogen bonding may be formed between the polysaccharide polymer 120 and the plurality of layered materials, so that the plurality of layered materials may be exfoliated into a single layer.

The polysaccharide polymer 120 and the transition metal-dichalcogenide compound (TMD) 110 may be mixed in a solvent to prepare a structure for bacterial detection 130, in which the transition metal-dichalcogenide compound 110 is exfoliated by the hydroxyl group 121 of the polysaccharide polymer 120 and the polysaccharide polymer 120 and the exfoliated transition metal-dichalcogenide compound 110 are bound (S120). According to one embodiment, the polysaccharide polymer 120 and the transition metal-dichalcogenide compound 110 may be mixed in a solvent to prepare a mixed solution, after which the mixed solution may be subject to ultrasonic treatment. For example, the mixed solution may be placed on an ice bath and may be subject to ultrasonic treatment by using a probe tip sonicator. The ultrasonic treatment of the mixed solution may be performed at 170 W for six seconds and then for five hours by providing a pulse at an interval of two seconds.

According to Example 1 of the present invention, in the exfoliating of the transition metal-dichalcogenide compound (bulk TMDs) 110 in a bulk state by the hydroxyl group 121 of the polysaccharide polymer 120, multivalent hydrogen bonding may be formed between the polysaccharide polymer 120 and the transition metal-dichalcogenide compound 110, since the polysaccharide polymer 120 contains the plurality of hydroxyl groups 121 as described above. Accordingly, the transition metal-dichalcogenide compound 110 in the bulk state may be exfoliated into a single layer. After the transition metal-dichalcogenide compound 110 in the bulk state is exfoliated, the structure for bacterial detection 130, in which the polysaccharide polymer 120 is bound to the exfoliated transition metal-dichalcogenide compound 110, may be prepared as shown in FIG. 2.

According to Example 1 of the present invention, the transition metal-dichalcogenide compound 110 may contain Mo and W as a transition metal element, and contain S and Se as a dichalcogenide element. Accordingly, the transition metal-dichalcogenide compound 110 according to Example 1 of the present invention may be $WS_2$, $WSe_2$, and $MoSe_2$. As described above, if the polysaccharide polymer 120 is dextran, the structure for bacterial detection 130 according to Example 1 of the present invention may be dex-$WS_2$, dex-$WSe_2$, and dex-$MoSe_2$.

According to one embodiment, the exfoliated transition metal-dichalcogenide compound 110 may have semiconductor properties, and thus the exfoliated transition metal-dichalcogenide compound 110 may have Raman scattering properties. Due to the Raman scattering properties of the exfoliated transition metal-dichalcogenide compound 110, a material bound to the exfoliated transition metal-dichalcogenide compound 110 can be easily detected.

An object to be detected may be bound to the polysaccharide polymer 120 of the structure for bacterial detection 130 (S130). According to Example 1 of the present invention, it may be possible to prepare the structure for bacterial detection 130 in which the transition metal-dichalcogenide compound 110 is exfoliated by the hydroxyl group 121 of the polysaccharide polymer 120 and the polysaccharide polymer 120 is bound to the exfoliated transition metal-dichalcogenide compound 110 as described above. In addition, the object to be detected may be bound to the polysaccharide polymer 120 of the structure for bacterial detection 130. In other words, the structure for bacterial detection 130 may have a structure including the polysaccharide polymer 120 bound to the object to be detected, and the exfoliated transition metal-dichalcogenide compound 110 bound to the polysaccharide polymer 120.

As described above, due to the Raman scattering properties of the exfoliated transition metal-dichalcogenide compound 110, the object to be detected, which is bound to the structure for bacterial detection 130, can be easily detected. In other words, since there is provided a structure in which the object to be detected and the exfoliated transition metal-dichalcogenide compound 110 are linked by the medium of the polysaccharide polymer 120, the object to be detected can be easily detected due to the Raman scattering properties of the exfoliated transition metal-dichalcogenide compound 110. For example, in case of Raman signal mapping of the object to be detected, which is bound to the structure for bacterial detection 130, by using Raman analysis, the object to be detected can be easily detected, since the Raman scattering properties of the exfoliated transition metal-dichalcogenide compound 110 of the structure for bacterial detection 130, which is bound to the object to be detected by the polysaccharide polymer 120 of the structure for bacterial detection 130, are shown as a signal.

According to Example 1 of the present invention, the structure for bacterial detection 130 may selectively detect the object to be detected. For example, if the object to be detected includes *Escherichia coli*, *Salmonella*, and *Staphylococcus aureus*, the structure for bacterial detection 130 according to Example 1 of the present invention may selectively detect *Escherichia coli*.

The method for preparing a structure for bacterial detection and the method for detecting bacteria according to Example 1 of the present invention have been described in detail. Hereinafter, a method for preparing a structure for microbe detection according to Example 2 of the present invention will be described by applying the method for preparing a structure for bacterial detection according to Example 1 of the present invention. The structure for microbe detection according to Example 2 of the present invention with Example 1 of the present invention applied may include at least one of the structure for bacterial detection according to Example 1 of the present invention, which is a structure in which the exfoliated transition metal-dichalcogenide compound 110 and the polysaccharide polymer 120 are bound, or the exfoliated transition metal-dichalcogenide compound 110.

FIG. 3 is a flow chart for explaining a method for preparing a structure for microbe detection according to Example 2 of the present invention. FIG. 4 is a view for explaining a method for preparing a first compound according to Example 2 of the present invention, FIG. 5 is a view for explaining a method for preparing a second compound according to Example 2 of the present invention, and FIG. 6 is a view for explaining a change in properties depending on pH of a second compound according to Example 2 of the present invention. FIG. 7 is a view for explaining a method for preparing a third compound according to Example 2 of the present invention, FIG. 8 is a view for explaining a method for preparing a structure for microbe detection according to Example 2 of the present invention, and FIG. 9 is a view for explaining a structure for microbe detection according to Example 2 of the present invention.

Referring to FIGS. 3 and 4, a first compound 230 may be prepared by reacting nitrilotriacetic acid (NTA) 210 and an acid anhydride 220 (S210). According to Example 2 of the present invention, the preparing of the first compound 230 may include: dissolving the nitrilotriacetic acid 210 in a solvent; adding and stirring the acid anhydride 220 and a non-nucleophilic basic material into the solvent in which the nitrilotriacetic acid 210 is dissolved, so as to prepare a mixed solution containing a preliminary first compound; adding an excessive amount of ester into the mixed solution to precipitate the preliminary first compound of the mixed solution; and washing and freeze-drying the precipitated preliminary first compound to prepare the first compound 230.

According to one embodiment, the nitrilotriacetic acid 210 has an affinity for metal ions 310, and thus may be easily bound with the metal ions 310 to form a compound. According to one embodiment, the acid anhydride 220 added into the nitrilotriacetic acid 210 may include at least one of succinic anhydride (SA), phthalic anhydride, or maleic anhydride. In addition, the non-nucleophilic basic material may include at least one of N,N-diisopropylethylamine (N,N-DIEA), 1,8-diazabicyclo[5.4.0]undec-7-ene, or 1,5-diazabicyclo[4.3.0]non-5-ene.

According to Example 2 of the present invention, if the acid anhydride 220 and the non-nucleophilic basic material are added and stirred into the solvent in which the nitrilotriacetic acid 210 is dissolved, protons of the nitrilotriacetic acid 210 may be removed by the non-nucleophilic basic material, and an amino group (—$NH_2$) of the nitrilotriacetic acid 210 with the protons removed may easily form a bond with electrons. Accordingly, the acid anhydride 220 may be easily bound to the amino group of the nitrilotriacetic acid 210 by the non-nucleophilic basic material, so as to prepare the mixed solution containing the preliminary first compound.

According to Example 2 of the present invention, the adding and stirring of the acid anhydride 220 and the non-nucleophilic basic material into the solvent in which the nitrilotriacetic acid 210 is dissolved may be performed for 18 hours. After the stirring, an excessive amount of the ester may be added. According to one embodiment, the ester may include ethyl acetate. According to one embodiment, the ester may dissolve impurities other than the preliminary first compound while not dissolving the preliminary first compound. Accordingly, the preliminary first compound contained in the mixed solution may be easily separated from the impurities other than the preliminary first compound contained in the mixed solution. In other words, the impurities other than the preliminary first compound contained in the mixed solution containing the preliminary first compound may be dissolved in the ester, but the preliminary first compound contained in the mixed solution may not be dissolved in the ester. Accordingly, the precipitated preliminary first compound may be easily separated by removing a liquid material of the mixed solution in which the impurities are dissolved, except for the preliminary first compound.

According to Example 2 of the present invention, the separating of the preliminary first compound and impurities of the mixed solution may be performed three times in total. The preliminary first compound separated from the impurities of the mixed solution may be washed and freeze-dried to prepare the first compound 230 according to Example 2 the present invention. Through the freeze-drying, the impurities remaining in the preliminary first compound may be removed to prepare the first compound 230 according to Example 2 of the present invention.

Referring to FIGS. 3 and 5, metal ions 310 may be bound to the first compound 230 to prepare a second compound 320 (S220). According to one embodiment, the metal ions 310 may be a divalent metal cation. For example, the metal ions 310 may include at least one of $Fe^{2+}$, $Cu^{2+}$, $Ni^{2+}$, $Co^{2+}$, or $Zn^{2+}$. Alternatively, according to another embodiment, the metal ions 310 may be a trivalent metal cation or a tetravalent metal cation.

The preparing of the second compound 320 may include dissolving the first compound 230 in a solvent and adding the metal ions 310. According to one embodiment, the solvent may be distilled water, and an amount of the solvent may be 11 mM. According to Example 2 of the present invention, the preparing of the second compound 320 may be performed at a pH in a range of more than 3.7 and less than 6.0.

Referring to FIG. 6, it may be possible to observe a change in properties depending on pH of the second compound 320 according to Example 2 of the present invention. For example, if the metal ion 310 of the second compound 320 is $Cu^{2+}$, it can be confirmed that a molar ratio of the $Cu^{2+}$ bound to the first compound at a pH of 5.5 is higher than a molar ratio of the $Cu^{2+}$ bound to the first compound at a pH of 3.7. However, if the preparing of the second compound 320 is performed at a pH in the range of 6.0 or higher, an aggregate containing the first compound 230 and the metal ions 310 may be formed, and thus a reaction for forming the second compound 320 may become unstable. However, according to Example 2 of the present invention, the second compound 320 may be prepared at a pH in the range of more than 3.7 and less than 6.0 as described above, thereby preventing the aggregate from being formed and thereby preparing the second compound 320 with a stable reaction.

As described above in step S210, according to Example 2 of the present invention, the nitrilotriacetic acid 210 has an affinity for the metal ions 310, and thus the nitrilotriacetic acid 210 of the first compound 230 may be easily bound with the metal ions 310 to prepare the second compound 320.

Referring to FIGS. 3 and 7, a third compound 420 may be prepared by binding the second compound 320 and a microbe detector 410 (S230). According to Example 2 of the present invention, the preparing of the third compound 420 may include adding a cross-linking agent including carbodiimide into the second compound 320, and adding and stirring the microbe detector 410 into the second compound 320 to which the cross-linking agent is added. As described above in step S220, the first compound 230 is dissolved in a solvent and the metal ions 310 are added to prepare the second compound 320. Thus, in the preparing of the third compound 420, the second compound 320 may be present in a state of solution. In addition, as described above, a pH of the solution may be in a range of more than 3.7 and less than 6.0.

According to Example 2 of the present invention, the cross-linking agent including the carbodiimide may be added into the second compound 320 in a state of solution. According to one embodiment, the cross-linking agent including the carbodiimide may include at least one of 1-ethyl-3-(3-dimethylaminopropyl)carbodiimide (EDC), dicyclohexylcarbodiimide, or N,N'-diisopropylcarbodiimide. The carbodiimide of the cross-linking agent may serve to conjugate a carboxy group (—COOH) and an amino group. Accordingly, the carboxyl group may be activated by the carbodiimide of the cross-linking agent so as to produce an O-acylisourea intermediate, and cause a reaction with amine of the microbe detector 410. In other words, the microbe detector 410 may be substituted in a place of the cross-linking agent of the structure in which the cross-linking agent including the carbodiimide is bound to the second compound 320, so as to prepare a third compound 420 according to an embodiment of the present invention. In other words, the cross-linking agent is added into the second compound 320, and thus the second compound 320 and the microbe detector 410 may be easily bound to each other.

According to Example 2 of the present invention, the adding of the cross-linking agent into the second compound 320 may include adding an activation material of the cross-linking agent in addition to the cross-linking agent. According to one embodiment, the activation material of the cross-linking agent may include at least one of N-hydroxysuccinimide (NHS) or sulfo-N-hydroxysuccinimide (sulfo-NHS). The activation material of the cross-linking agent may serve to stably activate the cross-linking agent including the carbodiimide. In other words, the activation material may stably activate a process in which the carbodiimide of the cross-linking agent conjugates the carboxy group and the amino group. As described above, in case of adding the activation material according to Example 2 of the present invention in the activating of the carboxy group by the carbodiimide to produce the O-acylisourea intermediate, N-hydroxysuccinimide (NHS) ester that is more stable than the O-acylisourea intermediate may be produced by the activation material. Accordingly, rather than adding the cross-linking agent alone into the second compound 320, in case of adding the cross-linking agent and adding the activation material of the cross-linking agent, the second compound 320 and the microbe detector 410 can be easily bound. According to Example 2 of the present invention, the adding of the activation material of the cross-linking agent may be performed as a series of processes of adding the cross-linking agent and adding the activation material, the N-hydroxysuccinimide ester may be formed, and thus the carbodiimide of the cross-linking agent may be stably activated to conjugate the carboxy group and the amino group, and thus the second compound 320 and the microbe detector 410 may be easily bound.

According to Example 2 of the present invention, the microbe detector 410 may include at least one of biomolecules including peptide, DNA or RNA.

Referring to FIGS. 3 and 8, the exfoliated transition metal-dichalcogenide compound 110 and the third compound 420 may be mixed to prepare a structure for microbe detection 510, in which the metal ions 310 of the third compound 420 are bound with the transition metal-dichalcogenide compound 110 (S240). According to Example 2 of the present invention, as described above in steps S110 and S120, a polysaccharide polymer 120 containing a hydroxyl group 121 may be provided, and the polysaccharide polymer 120 and the transition metal-dichalcogenide compound 110 may be mixed in a solvent to prepare the transition metal-dichalcogenide compound 110 which is exfoliated by the hydroxyl group 121 of the polysaccharide polymer 120. According to one embodiment, the mixing of the exfoliated transition metal-dichalcogenide compound 110 and the third compound 420 may include adding the exfoliated transition metal-dichalcogenide compound 110 into the solvent to prepare a mixed solution and adding the third compound 420 into the mixed solution. Since the third compound 420 is added into the mixed solution and then stirred, it may be possible to prepare a structure for microbe detection 510 according to Example 2 of the present invention, in which the metal ions 310 of the third compound 420 are bound with the exfoliated transition metal-dichalcogenide compound 110.

According to Example 2 of the present invention, as described above, for example, the transition metal-dichalcogenide compound 110 may contain Mo and W as the transition metal element, and the S and Se as the dichalcogenide element. Accordingly, the transition metal-dichalcogenide compound 110 according to Example 2 of the present invention may be $WS_2$, $WSe_2$, and $MoSe_2$. In addition, as described above, the metal ions 310 may include at least one of $Fe^{2+}$, $Cu^{2+}$, $Ni^{2+}$, $Co^{2+}$, or $Zn^{2+}$. For example, if the metal ion 310 is $Cu^{2+}$, the structure for microbe detection 510 according to Example 2 of the present invention may be $WS_2$-Cu-AA, $WSe_2$-Cu-AA, and $MoSe_2$-Cu-AA. The "AA" of the structure for microbe detection 510 may be the microbe detector 410 of the structure for microbe detection 510. According to Example 2 of the present invention, the may include at least one of biomolecules including peptide, DNA or RNA.

Referring to FIG. 9, as described above, the structure for microbe detection 510 according to Example 2 of the present invention can be prepared by using the method for preparing a structure for microbe detection 510 according to Example 2 of the present invention. As described above, the structure for microbe detection 510 according to Example 2 of the present invention may include the exfoliated transition metal-dichalcogenide compound 110 and the compound for microbe detection bound with the transition metal-dichalcogenide compound 110. However, the compound for microbe detection may contain the metal ions 310 bound to the transition metal-dichalcogenide compound 110, the nitrilotriacetic acid 210 bound to the metal ions 310, and the microbe detector 410 bound to the nitrilotriacetic acid 210.

According to Example 2 of the present invention, as described above, the microbes bound to the structure for microbe detection 510 can be easily detected due to the Raman scattering properties of the exfoliated transition metal-dichalcogenide compound 110. In other words, there may be provided a structure in which the transition metal-dichalcogenide compound 110 and the microbe detector 410 are linked (that is, a structure in which TMD-metal ion-NTA-microbe detector are linked) by the medium of the metal ions 310 and the nitrilotriacetic acid 210. Accordingly, it may be possible to easily detect the microbe selectively bound to the microbe detector 410 by using the Raman scattering properties of the exfoliated transition metal-dichalcogenide compound 110 (that is, the microbe is selectively bound to the microbe detector of the structure for microbe detection including a structure in which the TMD-metal ion-NTA-microbe detector are linked). For example, in a state in which the microbe is bound to the microbe detector 410 of the structure for microbe detection 510, when Raman signal mapping is performed using Raman analysis, the Raman scattering properties of the exfoliated transition metal-dichalcogenide compound 110 is shown as a signal, and thus the microbe can be easily detected.

According to Example 2 of the present invention, the detection may be performed in such a way that a microbe including at least one of *Escherichia coli* or *Salmonella* is bound to the microbe detector 410 of the structure for microbe detection 510.

The method for preparing the structure for microbe detection and the method for detecting microbes according to Example 2 of the present invention have been described in detail. Hereinafter, specific experimental examples will be described with regard to a method for preparing a structure for bacterial detection according to Example 1 of the present invention as described above.

Method for Preparing a Structure for Bacterial Detection According to Experimental Example 1-1

Dextran was provided as a polysaccharide polymer containing a hydroxyl group.

$WS_2$ was provided as a transition metal-dichalcogenide compound.

The dextran and $WS_2$ were added and mixed into distilled water to prepare a mixed solution.

The mixed solution was placed on an ice bath, was subject to ultrasonic treatment at 170 W for six seconds by using a probe tip sonicator, and then was subject to ultrasonic treatment for five hours by providing a pulse at an interval of two seconds, so as to prepare a structure for bacterial detection (dex-$WS_2$) according to Experimental Example 1-1 of the present invention.

Method for Preparing a Structure for Bacterial Detection According to Experimental Example 1-2

A structure for bacterial detection was prepared by the same method as described above in Experimental Example 1-1. However, $WSe_2$ was provided as the transition metal-dichalcogenide compound, so as to prepare a structure for bacterial detection (dex-$WSe_2$) according to Experimental Example 1-2 of the present invention.

Method for Preparing a Structure for Bacterial Detection According to Experimental Example 1-3

A structure for bacterial detection was prepared by the same method as described above in Experimental Example 1-1. However, $MoSe_2$ was provided as the transition metal-dichalcogenide compound, so as to prepare a structure for bacterial detection (dex-$MoSe_2$) according to Experimental Example 1-3 of the present invention.

Experimental examples on a method for preparing a structure for bacterial detection according to Example 1 of the present invention may be summarized as shown in the following [Table 1].

TABLE 1

| | Structure for bacterial detection |
|---|---|
| Experimental Example 1-1 | dex-$WS_2$ |
| Experimental Example 1-2 | dex-$WSe_2$ |
| Experimental Example 1-3 | dex-$MoSe_2$ |

FIG. 10 is a view showing pictures for explaining a method for preparing a structure for bacterial detection according to Experimental Examples 1-1 to 1-3 of the present invention, FIG. 11 is a view showing transmission electron microscope (TEM) pictures of a structure for bacterial detection according to Experimental Examples 1-1 to 1-3 of the present invention, and FIG. 12 is a view showing results of measuring a thickness of a structure for bacterial detection according to Experimental Examples 1-1 to 1-3 of the present invention.

Referring to FIG. 10, in case of mixing a polysaccharide polymer containing a hydroxyl group, which is dextran, and the transition metal-dichalcogenide compound in a solvent according to the method for preparing a structure for bacterial detection in accordance with Experimental Examples 1-1 to 1-3 of the present invention, it can be confirmed that the transition metal-dichalcogenide compound is exfoliated by the dextran and the solvent, which used to be colorless before mixing the dextran, is changed into a dark color by containing the transition metal-dichalcogenide compound.

In contrast, in case of mixing a material other than the dextran to exfoliate the transition metal-dichalcogenide compound, it can be confirmed from FIG. 10 that the transition metal-dichalcogenide compound is not exfoliated, or the transition metal-dicalcogenide compound is insignificantly exfoliated, if any. In other words, in case of mixing glucose and the transition metal-dichalcogenide compound in the solvent to exfoliate the transition metal-dichalcogenide compound, it can be confirmed that the transition metal-dichalcogenide compound is not exfoliated and thus the solvent remains colorless. In addition, in case of mixing polyethylene glycol (PEG) and the transition metal-dichalcogenide compound in the solvent, it can be confirmed that the transition metal-dichalcogenide compound is insignificantly exfoliated and thus a color of the solvent is insignificantly changed.

Referring to FIG. 11, it may be possible to observe the size and distribution of the structure for bacterial detection according to Experimental Examples 1-1 to 1-3 of the present invention. Referring to FIG. 12, it may be possible to observe the thickness of the structure for bacterial detection according to Experimental Examples 1-1 to 1-3 of the present invention. Through FIGS. 11 and 12, it can be confirmed that the structure for bacterial detection according to Experimental Examples 1-1 to 1-3 of the present invention is formed into a single layer since the transition metal-dichalcogenide compound is exfoliated according to the method for preparing the structure for bacterial detection according to Example 1 of the present invention.

FIG. 13 is a graph showing an UV-Vis absorbance of a structure for bacterial detection according to Experimental Examples 1-1 to 1-3 of the present invention, FIG. 14 is a graph showing Raman scattering of a structure for bacterial detection according to Experimental Examples 1-1 to 1-3 of the present invention, and FIG. 15 is a graph showing fluorescence spectra of structures for bacterial detection according to Experimental Examples 1-1 to 1-3 of the present invention.

Referring to FIGS. 13 to 15, it can be confirmed that the structure for bacterial detection according to Experimental Examples 1-1 to 1-3 of the present invention includes the exfoliated transition metal-dichalcogenide compound, and thus shows optical properties of the exfoliated transition metal-dichalcogenide compound unlike the transition metal-dichalcogenide compound in a bulk state. In other words, it can be understood that the structure for bacterial detection according to Experimental Examples 1-1 to 1-3 of the present invention includes the exfoliated transition metal-dichalcogenide compound, and thus loses the optical properties of the transition metal-dichalcogenide compound in the bulk state before being exfoliated, but shows the optical properties of the exfoliated transition metal-dichalcogenide compound as shown in FIGS. 13 to 15.

FIG. 16 is an image showing two-dimensional fluorescence signal mapping of a structure for bacterial detection according to Experimental Examples 1-1 to 1-3 of the present invention.

Referring to FIG. 16, the two-dimensional fluorescence signal mapping was performed by using a laser of 532 nm, and it can be confirmed that the structure for bacterial detection according to Experimental Examples 1-1 to 1-3 of the present invention includes the transition metal-dichalcogenide compound in which the transition metal-dichalcogenide compound is exfoliated and formed into a single layer.

FIG. 17 is a view showing FT-IR spectra of structures for bacterial detection according to Experimental Example 1-1 of the present invention, and FIG. 18 is a graph showing a measured absorbance of a structure for bacterial detection according to Experimental Example 1-1 of the present invention.

Referring to FIG. 17, it may be possible to confirm the binding properties of the transition metal-dichalcogenide compound and dextran with regard to the structure for bacterial detection according to Experimental Example 1-1 of the present invention. In the FT-IR spectra of FIG. 17, a transmittance was observed at 1004 cm$^{-1}$ before binding the transition metal-dichalcogenide compound and dextran, and the transmittance was shifted to 1021 cm$^{-1}$ after binding the transition metal-dichalcogenide compound and dextran. Accordingly, it can be understood that the transition metal-dichalcogenide compound and dextran were bound to prepare a structure for bacterial detection according to Experimental Example 1-1 of the present invention.

Referring to FIG. 18, it may be possible to confirm the binding stability of the transition metal-dichalcogenide compound and dextran with regard to the structure for bacterial detection according to Experimental Example 1-1 of the present invention. In order to confirm the binding stability of the transition metal-dichalcogenide compound and dextran, a change in absorbance of the structure according to Experimental Example 1-1 of the present invention was observed by repeatedly carrying out centrifugation and dispersion with regard to the structure according to Experimental Example 1-1 of the present invention, in which the transition metal-dichalcogenide compound and dextran are bound. In the above graph of FIG. 18, there was no change in absorbance properties even after repeatedly carrying out centrifugation and dispersion with regard to the structure according to Experimental Example 1-1 of the present invention, and thus it can be understood that a bond is stably formed in the structure for bacterial detection according to Experimental Example 1-1 of the present invention.

FIG. 19 is a view for explaining a method for detecting bacteria by using a structure for bacterial detection according to Example 1 of the present invention.

Referring to FIG. 19, as described above, the bacteria bound to the structure for bacterial detection according to Example 1 of the present invention can be easily detected due to the Raman scattering properties of the exfoliated transition metal-dichalcogenide compound. In other words, since there is provided a structure in which the bacteria and the transition metal-dichalcogenide compound are linked by the medium of the dextran, the bacteria can be detected due to the Raman scattering properties of the exfoliated transition metal-dichalcogenide compound. For example, in case of Raman signal mapping of the bacteria bound to the structure for bacterial detection according to Example 1 of the present invention by using Raman analysis, the Raman scattering properties of the exfoliated transition metal-dichalcogenide compound of the structure for bacterial detection according to Example 1 of the present invention, which is bound to the bacteria, are shown as a signal, and thus the bacteria can be easily detected.

FIG. 20 in (a) is an optical image showing bacteria detected by using a structure for bacterial detection according to Example 1-1 of the present invention, FIG. 20 in (b) is a view showing mapping of bacteria using Raman analysis, which are detected by using a structure for bacterial detection according to Experimental Example 1-1 of the present invention, and FIG. 21 is a graph showing Raman signal intensity of bacteria detected by using a structure for bacterial detection according to Experimental Example 1-1 of the present invention.

Referring to FIG. 20 in (a) and (b), it can be confirmed that the structure for bacterial detection according to Experimental Example 1-1 of the present invention is used for detecting the three kinds of bacteria. The three kinds of bacteria may include *Escherichia coli, Salmonella*, and *Staphylococcus aureus*. If the structure for bacterial detection according to Experimental Example 1-1 of the present invention is used for detecting the three kinds of bacteria, as shown in FIG. 20 in (b), the structure for bacterial detection according to Experimental Example 1-1 of the present invention, which is bound to the *Escherichia coli*, shows a Raman scattering signal, and thus it can be confirmed that the structure for bacterial detection according to Experimental Example 1-1 of the present invention selectively detects the *Escherichia coli*. In addition, referring to FIG. 21, the structure for bacterial detection according to Experimental Example 1-1 of the present invention, which is bound to the *Escherichia coli* out of the three kinds of bacterial, shows the highest Raman signal intensity, and thus it can be confirmed that the structure for bacterial detection according to Experimental Example 1-1 of the present invention selectively detects the *Escherichia coli*.

FIG. 22 in (a) is an optical image of *Escherichia coli, Salmonella*, and *Staphylococcus aureus*, and FIG. 22 in (b) is a view showing Raman mapping of bacteria detected by using a structure for bacterial detection according to Experimental Example 1-1 of the present invention.

Referring to FIG. 22 in (a) and (b), it can be confirmed that the structure for bacterial detection according to Experimental Example 1-1 of the present invention detects a singular number of bacteria. In particular, as described above, it can be confirmed that the structure for bacterial detection according to Experimental Example 1-1 of the present invention can selectively detect the *Escherichia coli* and selectively detect even a singular number of the *Escherichia coli*.

FIG. 23 in (a) and (b) are views showing SEM pictures of *Escherichia coli*, and FIG. 24 in (a) and (b) are views showing SEM pictures of *Escherichia coli* detected by using a structure for bacterial detection according to Experimental Example 1-1 of the present invention.

Referring to FIG. 23 in (a) and (b), it can be confirmed that the *Escherichia coli* has a clear surface without an unevenness before binding with the structure for bacterial detection according to Experimental Example 1-1 of the present invention. In contrast, referring to FIG. 24 in (a) and (b), it can be observed that a surface of the *Escherichia coli* bound with the structure for bacterial detection according to Experimental Example 1-1 of the present invention shows an unevenness shape since the *Escherichia coli* and the structure for bacterial detection according to Experimental Example 1-1 of the present invention are bound.

With regard to the method for preparing the structure for bacterial detection as described in Example 1 of the present invention, specific experimental examples have been described in detail through Experimental Examples 1-1 to 1-3 of the present invention. Hereinafter, specific experimental examples will be described with regard to the method for preparing the structure for microbe detection as described in Example 2 embodiment of the present invention.

Method for Preparing a Structure for Microbe Detection According to Experimental Example 2-1

Nitrilotriacetic acid (NTA) was added and dissolved into a flask containing dimethyl sulfoxide, so as to prepare a first mixed solution.

Succinic anhydride (SA) was provided as an acid anhydride, and N,N-diisopropylethylamine (N,N-DIEA) was provided as a non-nucleophilic basic material.

The succinic anhydride and N,N-diisopropylethylamine were added into the first mixed solution, and stirred at room temperature for 18 hours, so as to prepare a second mixed solution containing a preliminary first compound.

An excessive amount of ethyl acetate was added into the second mixed solution containing the preliminary first compound to precipitate the preliminary first compound of the second mixed solution and separate impurities therefrom.

The separating of the preliminary first compound and impurities from the second mixed solution was performed three times in total.

The precipitated preliminary first compound was washed and freeze-dried to prepare a first compound (NTA-SA) in which the nitrilotriacetic acid and the succinic anhydride of the second mixed solution were bound to each other.

$Cu^{2+}$ was provided as a metal ion.

The first compound was dissolved in distilled water, and the $Cu^{2+}$ was added to prepare a third mixed solution.

The third mixed solution was maintained at a pH of 5.5, and stirred at room temperature for one hour to prepare a second compound (Cu-NTA) in which the $Cu^{2+}$ of the third mixed solution and the nitrilotriacetic acid of the first compound are bound to each other.

The second compound in a state of solution was maintained at a pH of 5.5, 1-ethyl-3-(3-dimethylaminopropyl) carbodiimide (EDC) was added as a cross-linking agent including carbodiimide into the second compound, and N-hydroxysuccinimide (NHS) was added as an activation material of the cross-linking agent, and stirred for 30 minutes to prepare a fourth mixed solution.

Tripeptide (AA) was provided as a microbe detector.

The tripeptide was added into the fourth mixed solution to prepare a third compound (Cu-AA) in which the $Cu^{2+}$ of the second compound and the tripeptide of the fourth mixed solution were bound to each other.

$WS_2$ was provided as an exfoliated transition metal-dichalcogenide compound (TMD).

The $WS_2$ and the third compound were added into distilled water, and stirred at room temperature for 24 hours to prepare a fifth mixed solution.

The fifth mixed solution was centrifuged to prepare the structure for microbe detection ($WS_2$-Cu-AA) according to Experimental Example 2-1 of the present invention, in which the $WS_2$ of the fifth mixed solution and the $Cu^{2+}$ of the third compound were bound to each other.

Method for Preparing a Structure for Microbe Detection According to Experimental Example 2-2

A structure for microbe detection was prepared by the same method as described above in Experimental Example 2-1. However, $WSe_2$ was provided as the exfoliated transition metal-dichalcogenide compound.

The $WSe_2$ and the third compound were added into distilled water, and stirred at 60° C. for four hours so as to prepare a sixth mixed solution.

The sixth mixed solution was centrifuged to prepare the structure for microbe detection ($WSe_2$-Cu-AA) according to Experimental Example 2-2 of the present invention, in which the $WSe_2$ of the sixth mixed solution and the $Cu^{2+}$ of the third compound were bound to each other.

Method for Preparing a Structure for Microbe Detection According to Experimental Example 2-3

A structure for microbe detection was prepared by the same method as described above in Experimental Example 2-1. However, $MoSe_2$ was provided as the exfoliated transition metal-dichalcogenide compound.

The $MoSe_2$ and the third compound were added into distilled water, and stirred at 60° C. for four hours so as to prepare a seventh mixed solution.

The seventh mixed solution was centrifuged to prepare the structure for microbe detection ($MoSe_2$-Cu-AA) according to Experimental Example 2-3 of the present invention, in which the $MoSe_2$ of the seventh mixed solution and the $Cu^{2+}$ of the third compound were bound to each other.

Experimental examples on a method for preparing a structure for microbe detection according to Example 2 of the present invention may be summarized as shown in the following [Table 2].

TABLE 2

| | Structure for microbe detection |
|---|---|
| Experimental Example 2-1 | $WS_2$-Cu-AA |
| Experimental Example 2-2 | $WSe_2$-Cu-AA |
| Experimental Example 2-3 | $MoSe_2$-Cu-AA |

FIG. 25 is a graph showing an UV-Vis absorbance of a structure for microbe detection according to Experimental Example 2-1 of the present invention, FIG. 26 is a graph showing Raman scattering of a structure for microbe detection according to Experimental Example 2-1 of the present invention, and FIG. 27 is a graph showing fluorescence spectra of structures for microbe detection according to Experimental Example 2-1 of the present invention.

Referring to FIG. 25, if the structure for microbe detection according to Experimental Example 2-1 of the present invention contains CHC, which is one of the tripeptides, it can be confirmed that the absorbance intensity of the exfoliated $WS_2$ and the absorbance intensity of the structure for microbe detection according to Experimental Example 2-1 of the present invention show similar properties. In addition, referring to FIG. 26, if the structure for microbe detection according to Experimental Example 2-1 of the present invention contains the CHC, it can be confirmed that a Raman signal intensity of the exfoliated $WS_2$ and a Raman signal intensity of the structure for microbe detection according to Experimental Example 2-1 of the present invention show similar properties. Accordingly, even if the structure for microbe detection according to Experimental Example 2-1 of the present invention contains the CHC, it can be understood that the absorbance intensity and Raman signal intensity properties of the exfoliated $WS_2$ are maintained.

In contrast, referring to FIG. 27, if the structure for microbe detection according to Experimental Example 2-1 of the present invention contains the CHC, it can be confirmed that a fluorescence intensity of the structure for microbe detection according to Experimental Example 2-1 of the present invention is very low compared to a fluorescence intensity of the exfoliated $WS_2$. Accordingly, if the structure for microbe detection according to Experimental Example 2-1 of the present invention contains the CHC, it can be understood that the fluorescence properties of the exfoliated $WS_2$ are lost.

FIG. 28 is a graph for explaining an amount of introduced various metal ions bound to a structure for microbe detection in a method for preparing a structure for microbe detection according to Example 2 of the present invention.

Referring to FIG. 28, the structure for microbe detection, to which various metal ions are bound, were prepared by using the method for preparing a structure for microbe detection according to Example 2 of the present invention, and ICP quantitative analysis was performed for the prepared structure for microbe detection. A divalent metal cations including $Fe^{2+}$, $Cu^{2+}$, $Ni^{2+}$, $Co^{2+}$, and $Zn^{2+}$ were used as the various metal ions. A ratio of the metal ions bound to $WS_2$ was calculated through the ICP quantitative analysis, thereby predicting a degree at which the various metal ions and $WS_2$ are bound. As shown in FIG. 28, the various metal ions including $Fe^{2+}$, $Cu^{2+}$, $Ni^{2+}$, $Co^{2+}$, and $Zn^{2+}$ may be used to prepare the structure for microbe detection according to Example 2 of the present invention. In case of preparing the structure for microbe detection according to Experimental Example 2-1 of the present invention, to which $Cu^{2+}$ is added, it can be confirmed that a concentration of a second compound containing the $Cu^{2+}$ is about 20%.

FIG. 29 is a view for explaining a method for detecting microbes by using a structure for microbe detection according to Example 2 of the present invention.

Referring to FIG. 29, as described above, the microbe, which is bound to the structure for microbe detection according to Example 2 of the present invention, can be easily detected due to the Raman scattering properties of the exfoliated transition metal-dichalcogenide compound. In other words, there may be provided a structure in which the transition metal-dichalcogenide compound and the microbe detector are linked (that is, a structure in which TMD-metal ion-NTA-microbe detector are linked) by the medium of the metal ions and the nitrilotriacetic acid. Accordingly, it may be possible to detect the microbe selectively bound to the microbe detector by using the Raman scattering properties of the exfoliated transition metal-dichalcogenide compound (that is, the microbe is selectively bound to the microbe detector of the structure for microbe detection including a structure in which the TMD-metal ion-NTA-microbe detector are linked). For example, in a state in which the microbe is bound to the microbe detector of the structure for microbe detection according to Example 2 of the present invention, when Raman signal mapping is performed by using Raman analysis, the Raman scattering properties of the exfoliated transition metal-dichalcogenide compound are shown as a signal, and thus the microbe can be easily detected.

FIG. 30 is a table showing two-dimensional mapping analysis of microbes detected by using a structure for microbe detection according to Experimental Example 2-1 of the present invention, FIG. 31 is a table showing two-dimensional mapping analysis of microbes detected by using a structure for microbe detection according to Experimental Example 2-2 of the present invention, and FIG. 32 is a table showing two-dimensional mapping analysis of microbes detected by using a structure for microbe detection according to Experimental Example 2-3 of the present invention.

Referring to FIGS. 30 to 32, it can be understood that the microbe is strongly bound to show a Raman signal, as a color is brighter in the two-dimensional mapping analysis table. As shown in FIG. 30, it can be confirmed that the structure for microbe detection according to Experimental Example 2-1 of the present invention is strongly bound to *Escherichia coli* and *Salmonella* and thus a color appears bright in the two-dimensional mapping analysis table. As shown in FIG. 31, it can be confirmed that the structure for microbe detection according to Experimental Example 2-2 of the present invention is strongly bound to *Escherichia coli*, also bound to *Salmonella*, and is insignificantly bound to *Staphylococcus aureus*. In addition, as shown in FIG. 32, it can be confirmed that the structure for microbe detection according to Experimental Example 2-3 of the present invention is bound to *Escherichia coli*, and is insignificantly bound to *Salmonella* and *Staphylococcus aureus*.

In addition, if the structure for microbe detection according to Experimental Example 2-1 of the present invention contains HAH, which is one of the tripeptides, it can be confirmed that the structure for microbe detection according to Experimental Example 2-1 of the present invention is selectively bound to *Escherichia coli*. And, if the structure for microbe detection according to Experimental Example 2-1 of the present invention contains CHC, which is one of the tripeptides, it can be confirmed that the structure for microbe detection according to Experimental Example 2-1 of the present invention is selectively bound to *Salmonella*. Accordingly, it can be understood that a specific microbe is selectively detectable by using the structure for microbe detection, to which various tripeptides are bound, according to Example 2 of the present invention.

FIG. 33 is a graph showing results of detecting microbes by using a structure for microbe detection according to Example 2 of the present invention.

Referring to FIG. 33, according to various types of tripeptide, normalization was performed based on the microbe having the strongest binding force to be bound to the structure for microbe detection according to Example 2 of the present invention, thereby calculating a difference from the microbe having the second strongest binding force to be bound to the structure for microbe detection according to Example 2 of the present invention. And the difference was represented by Max-Mid. If the structure for microbe detection according to Experimental Example 2-1 of the present invention contains the HAH, it can be confirmed from FIG. 33 that the structure for microbe detection according to Experimental Example 2-1 of the present invention is selectively bound to *Escherichia coli*. In addition, if the structure for microbe detection according to Experimental Example 2-1 of the present invention contains the CHC, it can be confirmed that the structure for microbe detection according to Experimental Example 2-1 of the present invention is selectively bound to *Salmonella*. Accordingly, it can be understood that the structure for microbe detection according to Example 2 of the present invention, to which various tripeptides are bound, is usable to selectively detect a specific microbe.

With regard to the method for preparing the structure for microbe detection as described in Example 2 of the present invention, specific experimental examples have been described in detail through Experimental Examples 2-1 to 2-3 of the present invention. Although the present invention has been described in detail with reference to exemplary embodiments and experimental examples, the scope of the present invention is not limited to a specific embodiment and should be interpreted by the attached claims. In addition, those skilled in the art will understand that many modifications and variations are available without departing from the scope of the present invention.

INDUSTRIAL APPLICABILITY

According to an embodiment of the present invention, the structure for microbe detection can be used to detect various microbes such as *Escherichia coli, Staphylococcus aureus, Salmonella* or the like.

The invention claimed is:
1. A method for manufacturing a structure for microbe detection, the method comprising:

reacting nitrilotriacetic acid (NTA) and an acid anhydride to prepare a first compound;
chelation of metal ions to the first compound to prepare a second compound;
binding the second compound and a microbe detector to prepare a third compound; and
mixing an exfoliated transition metal-dichalcogenide (TMD) compound and the third compound to prepare a structure for microbe detection, in which the metal ions of the third compound are bound with the transition metal-dichalcogenide compound.

2. The method of claim 1, wherein the preparing of the first compound comprises:
dissolving the nitrilotriacetic acid in a solvent;
adding and stirring the acid anhydride and a non-nucleophilic basic material into the solvent in which the nitrilotriacetic acid is dissolved, so as to prepare a mixed solution containing a preliminary first compound;
adding an excessive amount of ester into the mixed solution to precipitate the preliminary first compound of the mixed solution; and
washing and freeze-drying the precipitated preliminary first compound to prepare the first compound.

3. The method of claim 1, wherein the preparing of the second compound comprises dissolving the first compound in a solvent and adding the metal ions into a resulting solution.

4. The method of claim 3, wherein the preparing of the second compound is performed at pH in a range of more than 3.7 and less than 6.0.

5. The method of claim 3, wherein the preparing of the third compound comprises:
adding a cross-linking agent including carbodiimide into the second compound; and
adding and stirring the microbe detector into the second compound to which the cross-linking agent is added.

6. The method of claim 5, wherein the adding of the cross-linking agent into the second compound comprises adding an activation material of the cross-linking agent in addition to the cross-linking agent.

7. The method of claim 1, wherein the microbe detector comprises at least one of biomolecules including peptide, DNA or RNA.

* * * * *